(12) United States Patent  (10) Patent No.: US 9,103,758 B1
Frisch et al.  (45) Date of Patent: Aug. 11, 2015

(54) METHODS FOR FABRICATING TEST SPECIMEN ASSEMBLY HAVING WEAK ADHESIVE BONDS

(71) Applicant: The Boeing Company, Chicago, IL (US)

(72) Inventors: Douglas Allen Frisch, Renton, WA (US); Richard H. Bossi, Renton, WA (US); William Bruce Hopkins Grace, Vashon, WA (US); Marc Joel Piehl, Renton, WA (US); Kay Youngdahl Blohowiak, Issaquah, WA (US); Paul H. Shelley, Jr., Lakewood, WA (US)

(73) Assignee: THE BOEING COMPANY, Chicago, IL (US)

( * ) Notice: Subject to any disclaimer, the term of this patent is extended or adjusted under 35 U.S.C. 154(b) by 467 days.

(21) Appl. No.: 13/660,340

(22) Filed: Oct. 25, 2012

Related U.S. Application Data

(63) Continuation-in-part of application No. 12/908,032, filed on Oct. 20, 2010, now Pat. No. 8,342,017.

(51) Int. Cl.
*G01N 19/04* (2006.01)
*G01N 3/62* (2006.01)

(52) U.S. Cl.
CPC . *G01N 19/04* (2013.01); *G01N 3/62* (2013.01)

(58) Field of Classification Search
None
See application file for complete search history.

(56) References Cited

U.S. PATENT DOCUMENTS

| | | | | |
|---|---|---|---|---|
| 4,393,700 A | * | 7/1983 | Fabian | 73/150 A |
| 5,673,586 A | * | 10/1997 | Mann | 73/150 A |
| 5,705,752 A | * | 1/1998 | Chang et al. | 73/842 |
| 5,789,085 A | | 8/1998 | Blohowiak et al. | |
| 5,814,137 A | | 9/1998 | Blohowiak et al. | |
| 5,849,110 A | | 12/1998 | Blohowiak et al. | |
| 5,869,140 A | | 2/1999 | Blohowiak et al. | |
| 5,869,141 A | | 2/1999 | Blohowiak et al. | |
| 5,939,197 A | | 8/1999 | Blohowiak et al. | |
| 6,026,680 A | * | 2/2000 | Mann | 73/150 R |
| 6,037,060 A | | 3/2000 | Blohowiak et al. | |
| 6,551,407 B2 | | 4/2003 | Drzal et al. | |
| 6,565,927 B1 | | 5/2003 | Drzal et al. | |
| 6,581,446 B1 | * | 6/2003 | Deneuville et al. | 73/81 |
| 6,622,568 B2 | | 9/2003 | Nelson et al. | |
| 6,848,321 B2 | | 2/2005 | Bossi et al. | |

(Continued)

FOREIGN PATENT DOCUMENTS

EP 1367146 A2 3/2003
WO 2008127418 A2 10/2008

OTHER PUBLICATIONS

Dillingham et al., "Surface Preparation of Composite Materials for Adhesive Bonding," Proceedings of the 26th Annual Meeting of the Adhesion Society, Feb. 2003, 4 pages.

(Continued)

*Primary Examiner* — Andre Allen
(74) *Attorney, Agent, or Firm* — Yee & Associates, P.C.

(57) ABSTRACT

A method for manufacturing a test specimen assembly. A first material for the test specimen assembly and a witness coupon are positioned relative to each other. A surface treatment is applied onto a first surface of the first material and onto a surface of the witness coupon. An adhesive is applied onto the first surface of the first material. A second surface of a second material for the test specimen assembly is placed onto the first surface of the first material with the adhesive. The adhesive is cured to form the test specimen assembly.

20 Claims, 14 Drawing Sheets

(56) References Cited

U.S. PATENT DOCUMENTS

| | | | |
|---|---|---|---|
| 7,507,312 B2 | 3/2009 | Bossi et al. | |
| 7,509,876 B1 | 3/2009 | Sokol et al. | |
| 2008/0111027 A1 | 5/2008 | Blohowiak et al. | |
| 2008/0173098 A1* | 7/2008 | Liu et al. | 73/827 |
| 2013/0340534 A1* | 12/2013 | Gregg et al. | 73/826 |

OTHER PUBLICATIONS

Bossi et al., "Application of Stress Waves to Bond Inspection," SAMPE Conference, May 2004, 14 pages.

Bossi et al., "Composite Surface Preparation QA for Bonding," SAMPE Conference, May 2005, 12 Pages.

Bossi et al., "Laser Bond Testing," Materials Evaluation, vol. 67, No. 7, Jul. 2009, pp. 819-827.

Van Voast et al., "Effect of Varying Levels of Peel Ply Contamination on Adhesion Threshold," SAMPE Conference, May 2010, 16 pages.

Blohowiak et al., "Nonchemical Surface Treatments Using Energetic Systems for Structural Adhesive Bonding," SAMPE Conference, May 2010, 12 pages.

Van Voast et al., "Effect of Varying Levels of Peel Ply Contamination on Adhesion Threshold," PowerPoint presentation, SAMPE conference, May 2010, 38 pages.

Flinn, "Improving Adhesive Bonding of Composite Through Surface Characterization," PowerPoint presentation, The Joint Advanced Materials and Structures Center of Excellence, University of Washington, 26 pages.

Bossi et al., "Bond Strength Measurement Using a Laser Bond Inspection Device," SAMPE Conference, May 2004, 14 pages.

Flinn et al., "The Effect of Peel-Ply Surface Preparation Variables on Bond Quality," DOT/FAA/AR-06/28, Final Report, Aug. 2006, 35 pages.

Beth, "Laser Bond Inspection," LSP Technologies, Inc., Jun. 2011, 3 pages, accessed Oct. 22, 2012.

Markus et al, "Composite Bonds Put to the Test," SAE International Aerospace Engineering, Aug. 2012, 5 pages, accessed Jul. 26, 2012.

Bossi et al., "Methods for Fabricating Fiber-Reinforced Plastic Test Specimen Assembly Having Weak Adhesive Bonds," U.S. Appl. No. 12/908,032, filed Oct. 20, 2010, 49 pages.

USPTO office action dated Aug. 30, 2012 regarding U.S. Appl. No. 12/908,032, 6 pages.

Flinn et al., "Improving Adhesive Bonding of Composite Through Surface Characterization," PowerPoint Presentation, The Joint Advanced Materials and Structures Center of Excellence, University of Washington, 46 pages.

* cited by examiner

METHODS FOR FABRICATING TEST SPECIMEN ASSEMBLY HAVING WEAK ADHESIVE BONDS

CROSS-REFERENCE TO RELATED APPLICATION

This application is a continuation-in-part of co-pending patent application U.S. Ser. No. 12/908,032, filed on Oct. 20, 2010, entitled "Methods for Fabricating Fiber-Reinforced Plastic Test Specimen Assembly Having Weak Adhesive Bonds", which is incorporated herein by reference.

BACKGROUND INFORMATION

1. Field

The present disclosure relates generally to test specimens and in particular, to test specimens comprising adhesive bonds. Still more particularly, the present disclosure relates to methods for fabricating test specimens including methods for assembling a structure by adhesive bonding of respective composite or metal subcomponents. In particular, the present disclosure relates to methods for ensuring that the adhesive bond between two composite subcomponents, two metal subcomponents, or a metal subcomponent and a composite subcomponent has adequate strength.

2. Background

Adhesive bonding is an important joining method for aerospace structures. Strong, durable bonded joints are created by proper selection of the materials (adherends and adhesive), processing, assembly and cure. The certification of the bond requires that the strength be validated. Methods are needed to validate that bond strength measurement techniques are in calibration.

Validation of the bond strength involves a combination of process control validation and final bond quality validation. The development and implementation of bond quality validation, that returns an estimate of the bond strength, requires standards (also referred to herein as "test specimen assemblies") containing controlled levels of bond strength for calibration. A critical issue is that the weak bond standards be constructed without physical features or characteristics that can be detected by standard nondestructive inspection (NDI) methods such as ultrasound, infrared, shearography or x-ray. These standard NDI methods are performed on bonded structure to validate assembly issues and find unbonded regions. However, they are not necessarily capable of detecting weak bonds. Alternative inspection approaches for weak bond detection are needed and must be applicable to bonds that would be acceptable by the standard NDI processes. The standard needs to be constructed in a repeatable manner so that, as required, additional standards can be made. Further, the standard needs to possess variable strength bonds from weak to full strength. Finally the standard should be adaptable to the adherend thickness used in the actual construction of the adhesive joint of interest.

Such a standard would be useful for testing NDI methods of any type to determine whether the method is possibly sensitive to a weak bond interface. For the inspection methods that test for strength using loading of the bond in the testing, the standard will be mechanically failed as part of the testing and will therefore need to be replaced frequently.

Weak bonds have been found in practice due to variation in the manufacturing technique. In particular, incorrect material, surface preparation and contamination are key variables that can create weak bonds that are not detectable by NDI methods. Other processes, such as incorrect assembly or curing can result in features or material change effects that can be detected by NDI techniques. The creation of useful weak bond standards therefore resides in finding a controlled manner of degrading the interface for adhesion without creating features that are detectable by standard NDI methods. Thus the weak bond standards should represent the case of bonds that pass standard ultrasonic inspection but do not have full strength. It would be desirable to have a range of strengths such as one third, two thirds and full strength or 25, 50, 75 and 100% of full strength in the standards for calibration of the bond strength test method.

Weak bonds have been created in the past by adding chemical mixtures, distributing contaminates or disrupting a surface. Known methods of creating weak bonds can be difficult to repeat or will have features that can be detected by standard NDI methods. For example, poly film and aged adhesive methods can create weak interfaces, but the interface degradation is detectable by standard NDI methods. Variable grit blast methods have also been successful in creating variable strength bonds. The surface condition, however, is such that it is also possible with detailed inspections to detect the surface feature with standard NDI methods.

The problem to be solved was that, if a system were developed that could detect weak bonds, how could the system be calibrated and how would one know that it was operating correctly to detect a weak bond if one should exist. Therefore, it is desirable to have a method and apparatus that takes into account at least some of the issues discussed above, as well as other possible issues.

Therefore, it would be desirable to have a method and apparatus that takes into account at least some of the issues discussed above, as well as other possible issues.

SUMMARY

In an illustrative embodiment, a method for manufacturing a test specimen assembly is present. A first material for the test specimen assembly and a witness coupon are positioned relative to each other. A surface treatment is applied onto a first surface of the first material and onto a surface of the witness coupon. An adhesive is applied onto the first surface of the first material. A second surface of a second material for the test specimen assembly is placed onto the first surface of the first material with the adhesive. The adhesive is cured to form the test specimen assembly.

In another illustrative embodiment, a test specimen assembly comprises a first material, a second material, and an adhesive. The first material has a first surface. The first surface has a surface treatment. The second material has a second surface. The adhesive is located between the first surface of the first material and the second surface of the second material. The adhesive forms a bond between the first material and the second material. A strength of the bond is reduced from a desired strength for the bond when the surface treatment is absent from the first surface.

In yet another illustrative embodiment, a method for manufacturing a test specimen assembly is present. A surface treatment is applied onto a first surface of a first material for the test specimen assembly, the surface treatment selected from one of a contaminant, an etch, an etch that is heated, a sol-gel, a primer, and a release agent. A strength of a bond formed by an adhesive with the surface treatment is identified based on a number of characteristics of the surface treatment formed on the first surface. The adhesive is applied onto the first surface of the first material. A second surface of a second material for the test specimen assembly is placed onto the first surface of the first material with the adhesive. The adhesive is cured to form the test specimen assembly.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

Reference will hereinafter be made to the drawings in which similar elements in different drawings bear the same reference numerals.

DETAILED DESCRIPTION

Figure 1:
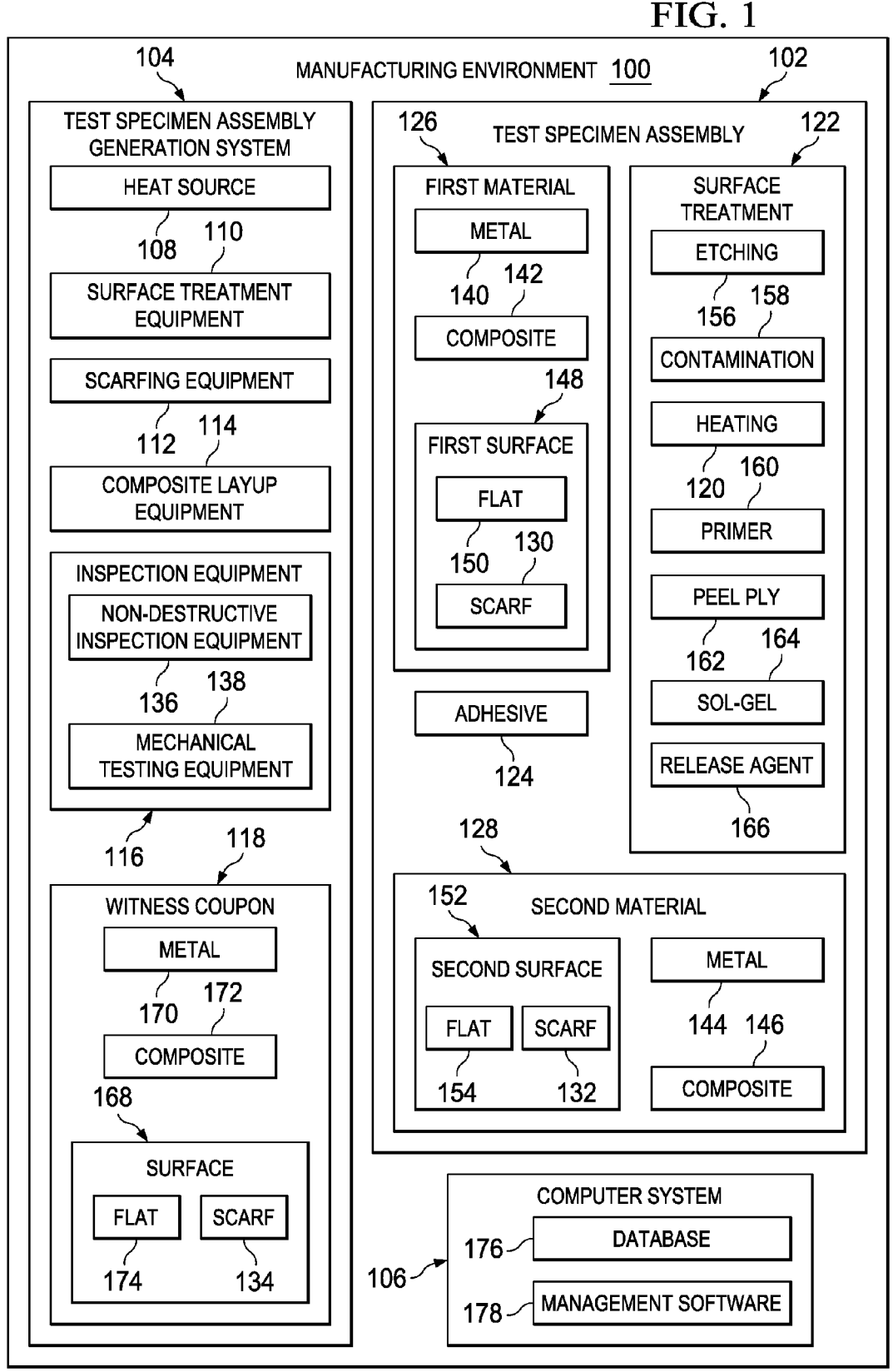
FIG. 1 is an illustration of a block diagram of a manufacturing environment in accordance with an illustrative embodiment.

One or more of the illustrative embodiments may solve the problems associated with weak bonds by providing manufactured standards, i.e., test specimen assemblies, having variable bond strengths which can be repeatedly duplicated for validating that a bond strength measurement system can in fact correctly detect a weak bond. Standards made in accordance with the methods disclosed herein can be used to validate that the certification method on a bonding process can in fact detect a weak (less than full strength) bond. A consistent bond is created that has variable strength but lacks features detectable by conventional NDI methods.

The illustrative embodiments may encompass various methods for repeatable surface preparation that can be used to manufacture weak bond standards having weak bond strengths not detectable by standard NDI techniques. The repeatable surface preparation techniques disclosed herein vary the activation of one of the surfaces to be bonded. The methods of manufacture disclosed herein can be used in any thickness of bond configuration based on the FRP thickness that it is applied to. Bonds created by these methods are indistinguishable in standard NDI examinations.

In some of the illustrative embodiments, a method is presented for fabricating a test specimen assembly comprising the following steps: (a) fabricating a first FRP test specimen having a bonding surface, wherein a first area of the bonding surface of the first FRP test specimen has a first bonded joint performance-governing characteristic, while a second area of the bonding surface, not overlapping with the first area, of the first FRP test specimen has a second bonded joint performance-governing characteristic different than the first bonded joint performance-governing characteristic; (b) fabricating a second FRP test specimen having a bonding surface; (c) placing the bonding surface of the first FRP test specimen in overlapping relationship with the bonding surface of the second FRP test specimen with adhesive therebetween, the adhesive being in contact with the first and second areas of the bonding surface of the first FRP test specimen and with the bonding surface of the second FRP test specimen; and (d) curing the adhesive to bond the first and second FRP test specimens together.

In accordance with some illustrative embodiments, the manufactured standard has variable bond strengths due to the use of different peel plies in the assembly. The method of manufacture uses a consistent product in the form of peel ply materials that are applied to the FRPs during the fabrication. Each peel ply type will result in a consistent surface type for bonding that will have different bond strength when assembled with the prescribed adhesive method.

In accordance with another illustrative embodiment, the standard is constructed using three different peel plies in each of three regions of one of the adherends to be adhesive bonded. When the other adherend is assembled to the adherend that was prepared with three different peel plies after removal of the latter, the resulting adhesive bond will have zones of three different bond strengths. The adhesive bond strengths will be consistent whenever the process is repeated because of the consistency of the peel ply materials.

In accordance with other illustrative embodiments, a commercially available peel ply material can be soaked for a controlled time in a concentrated bath containing release agent materials. By controlling the concentration and time, variable levels of peel ply contamination can be achieved.

In accordance with one specific embodiment, the standard is constructed using three peel plies in each of three regions of one of the adherends to be adhesive bonded, two of the peel plies having different levels of contamination by a release agent material and the third peel ply being uncontaminated. When the other adherend is assembled to the adherend that was prepared with three different peel plies, the resulting adhesive bond will have zones of three different bond strengths.

In accordance with other illustrative embodiments, the manufactured standard has variable bond strengths due to different surface treatments using energetic systems (such as systems for directing a plasma jet or a laser beam over a surface to be treated). In accordance with one such embodiment, a plasma jet is raster scanned over first and second areas of a first FRP test specimen under first and second sets of plasma conditions respectively. In accordance with another such embodiment, a laser beam is raster scanned over first and second areas of a first FRP test specimen under first and second sets of laser conditions respectively. When the differentially surface-treated first FRP test specimen and a second FRP test specimen are adhesively bonded, the result will be adhesive bonds of different strengths in the first and second areas.

With reference now to the figures and in particular with reference to FIG. 1, an illustration of a block diagram of a manufacturing environment is depicted in accordance with an illustrative embodiment. In FIG. 1, manufacturing environment 100 is an illustrative example of an environment in which the different illustrative embodiments may be implemented to form test specimen assembly 102.

As depicted, manufacturing environment 100 comprises test specimen assembly 102, test specimen assembly generation system 104, and computer system 106. Test specimen assembly generation system 104 is configured to form test specimen assembly 102. Specifically, test specimen assembly generation system 104 may perform at least one of forming, assembling, and processing of the different components of test specimen assembly 102.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C or item B and item C.

As depicted, test specimen assembly generation system 104 includes heat source 108, surface treatment equipment 110, scarfing equipment 112, composite layup equipment 114, inspection equipment 116, and witness coupon 118. Heat source 108 is configured to provide heat during formation of test specimen assembly 102. Further, heat source 108 may supply heating 120 as surface treatment 122 during formation of test specimen assembly 102. Heat source 108 may also be used to cure adhesive 124 of test specimen assembly 102. As depicted, heat source 108 may be selected from at least one of an oven, a heating patch, an autoclave, an iron, and other types of heating equipment.

Surface treatment equipment 110 is configured to apply surface treatment 122 during formation of test specimen assembly 102. Surface treatment equipment 110 is configured to apply surface treatment 122 to at least one of first material 126 of test specimen assembly 102, second material 128 of test specimen assembly 102, and witness coupon 118. Surface treatment equipment 110 may include, for example, at least one of a plasma generator, a laser system, a sprayer system, an aerosol system, a peel-ply application system, a liquid bath, or other suitable tooling for applying surface treatment 122.

In this illustrative example, scarfing equipment 112 is configured to remove layers of material during formation of test specimen assembly 102. By removing the layers of material, a number of layers are exposed. Scarfing equipment 112 may be used to generate at least one of scarf 130 of first material 126, scarf 132 of second material 128, or scarf 134 of witness coupon 118. Scarfing equipment 112 may comprise at least one of a grinder, a cutter, a sander, and any other tooling capable of exposing and sanding the layers of material.

Composite layup equipment 114 is configured to lay up layers of composite material during formation of test specimen assembly 102. Composite layup equipment 114 may be used to form at least one of first material 126 of test specimen assembly 102, second material 128 of test specimen assembly 102, or witness coupon 118. Composite layup equipment 114 may comprise winding equipment, a tape layup head, consolidation equipment, mandrels, and any other tooling capable of forming layers of composite material.

Inspection equipment 116 is configured to inspect materials during the formation of test specimen assembly 102. Inspection equipment 116 is also configured to inspect test specimen assembly 102 after formation. Inspection equipment 116 comprises non-destructive inspection equipment 136 and mechanical testing equipment 138. Mechanical testing equipment 138 may comprise a tensile strength tester, a DeFelsco® adhesive bond tester, a MIS@ servo-hydraulic test frame, or other suitable equipment.

Non-destructive inspection equipment 136 may comprise laser bond inspection equipment, ultrasound inspection equipment, infrared inspection equipment, shearography inspection equipment, optical inspection equipment, x-ray inspection equipment, and any other suitable inspection equipment. Conventional non-destructive inspection equipment includes ultrasound inspection equipment, infrared inspection equipment, shearography inspection equipment, optical inspection equipment, and x-ray inspection equipment. Laser bond inspection is nominally a non-destructive inspection because laser bond inspection does not fail bonds having sufficient strength. However, unlike conventional non-destructive inspection equipment, laser bond inspection may cause some bonds to fail. The laser bond inspection method uses high-intensity stress waves to create a tensile load at the bond interface. Increasing the power setting of the laser bond inspection equipment increases the tensile load at the bond surface. A bond having a lower strength than being tested for may fail due to the tensile load.

As depicted, test specimen assembly 102 includes first material 126, second material 128, surface treatment 122, and adhesive 124. In some cases, first material 126 and second material 128 may be referred to as test specimens. Adhesive 124 may be located between first material 126 and second material 128.

First material 126 may be comprised of a material selected from one of metal 140, composite 142, or some other suitable material. Composite 142 is created by combining two or more functional components. Further, composite 142 may include reinforcing fibers bound in a matrix. The fibers may take the form of at least one of fabrics, tape, tows, cloth, and other suitable forms. Additionally, the matrix may be a resin.

Second material 128 may be comprised of a material selected from one of metal 144, composite 146, or some other suitable material. Further, first material 126 and second material 128 may be comprised of the same material or different materials. For example, in one illustrative embodiment, first material 126 may comprise metal 140 and second material 128 comprises metal 144. In another illustrative embodiment, first material 126 and second material 128 may both comprise titanium.

In other illustrative embodiments, first material 126 comprises composite 142 and second material 128 comprises composite 146. In these illustrative embodiments, composite 142 and composite 146 may comprise the same or different composite materials. The composite materials may include, for example, without limitation a fiber reinforced plastic, glass-reinforced plastic, carbon-fiber-reinforced plastic, thermoplastic, a thermoset polymer, a composite polymer, and/or other types of composite materials.

In these illustrative examples, first material 126, second material 128, or both may be pre-fabricated. In other illustrative examples, first material 126, second material 128, or both may be formed in manufacturing environment 100. Composite layup equipment 114 may layup a number of layers of composite material to form first material 126, second material 128, or a portion of either first material 126 or second material 128.

A "number" as used herein with reference to items means one or more items. For example, a number of layers of composite material is one or more layers of composite material.

First material 126 has first surface 148. As depicted, first surface 148 may be flat 150 or have scarf 130. Scarf 130 is a reduction in thickness of first material 126. In scarf 130, a number of layers of first material 126 are exposed as a result of the reduction in thickness. Scarf 130 may expose all of the layers of first material 126 or only a portion of the number of layers of first material 126. Scarf 130 may comprise a surface with a slope that has a ratio of about 30:1. Scarf 130 may have other ratios for the slopes in other illustrative examples.

In one illustrative embodiment, scarfing equipment 112 may be used to generate scarf 130. Scarfing equipment 112 may comprise grinding equipment, cutting equipment, sanding equipment, and/or any other tooling capable of exposing and sanding first material 126. For example, scarfing equipment 112 may first expose the number of layers of first material 126. After exposing the number of layers of first material 126, scarfing equipment 112 may sand the exposed number of layers of first material 126. Accordingly, scarf 130 may include a number of exposed and sanded layers of the first material 126.

In another illustrative embodiment, first material 126 may comprise composite 142. In this illustrative example, composite layup equipment 114 may lay up a number of layers of composite 142 that gradually reduce in length to form scarf 130. By laying down composite layers in order of length, scarf 130 may be formed in first material 126.

In this illustrative example, second material 128 comprises second surface 152. Second surface 152 may be flat 154 or scarf 132 and may have substantially the same slope as first surface 148. If first surface and second surface 152 comprise substantially the same slope, the second surface may correspond to first surface 148 such that second surface 152 contacts first surface 148. The contact is such that gaps between first surface 148 and second surface 152 may be substantially absent. Composite layup equipment 114 may lay up layers of composite 146 to form scarf 132. Alternatively, scarfing equipment 112 may be used to form scarf 132.

In some illustrative examples, surface treatment 122 may be applied to first surface 148 of first material 126. Surface treatment 122 may comprise at least one of etching 156, contamination 158, heating 120, primer 160, peel ply 162, sol-gel 164, and release agent 166. Of course, in other illustrative examples, surface treatment may also be applied to at least one of second material 128 and witness coupon 118.

In the illustrative examples, applying a surface treatment means to cause the surface treatment to be formed on the surface of the material. For example, applying surface treatment 122 may include performing at least one of heating, etching, brushing, sputtering, spraying, depositing by chemical vapor deposition, and other mechanisms that cause the surface treatment to be formed on the surface of the material.

Surface treatment 122 reduces bond strength of test specimen assembly 102 from a desired strength. Desired strength is a bond strength formed by adhesive 124 in test specimen assembly 102 when surface treatment 122 is absent.

In the illustrative examples, bond strength may vary based on characteristics of surface treatment 122. Bond strength may be measured as a ratio of the desired strength for the bond when surface treatment 122 is absent from first surface 148. In the illustrative examples, the ratio may be, for example, about 0.75, about 0.5, about 0.25, about 0.66, about 0.33, or any other suitable ratio.

Bond strength may be identified directly, indirectly, or both indirectly and directly. In some illustrative embodiments, bond strength may be identified indirectly based on surface treatment 122. Indirect identification results from a measurement of a quantity that is different from the desired quantity. In these illustrative examples, the desired quantity is bond strength. When a known relationship links bond strength to another quantity, bond strength may be determined from measuring the other quantity.

In one illustrative embodiment, bond strength may be identified indirectly by characteristics of surface treatment 122. Characteristics of surface treatment 122 may be identified in a variety of ways. In some illustrative embodiments, surface treatment 122 is inspected using inspection equipment 116 to identify characteristics of surface treatment 122. Inspection equipment 116 may be used to inspect surface treatment 122 on at least one of first surface 148 of first material 126, surface 168 of witness coupon 118, and second surface 150 of second material 128.

In other illustrative embodiments, parameters used by surface treatment equipment 110 are analyzed to identify characteristics of surface treatment 122. Parameters used by surface treatment equipment 110 for the application of surface treatment 122 may be recorded. Parameters may include at least one of dose, volume, time, duration, and other suitable parameters for application of surface treatment 122.

In other illustrative embodiments, bond strength may be identified directly. Direct identification results from measuring a load on a bond which results in failure of the bond. This identification may be made by mechanically testing test specimen assembly 102. Mechanical tests may include at least one of a lap shear test, a double cantilever beam test, a flat-wise tension test, and any other suitable tests. Mechanical testing may be performed by mechanical testing equipment 138 of inspection equipment 116.

In the illustrative examples, surface treatment 122 is applied to first surface 148 of first material 126. Further, surface treatment 122 may also be applied to surface 168 of witness coupon 118 at substantially the same time.

As depicted, witness coupon 118 may be comprised of a material selected from one of metal 170, composite 172, and other suitable materials. In one illustrative example, witness coupon 118 may be comprised of the same material as first material 126. In another illustrative example, witness coupon 118 may be comprised of the same material as second material 128. In yet another illustrative example, witness coupon 118 may be comprised of a different material. This different material may be, for example, a polished metal.

As depicted, witness coupon 118 may have surface 168 that is flat 174, has scarf 134, or a combination of the two. Surface 168 of witness coupon 118 may have substantially the same surface slope as first surface 148 of first material 126. Thickness of witness coupon 118 may be substantially the same as thickness of first material 126. If witness coupon 118 and first material 126 have substantially the same surface slope and substantially the same thickness, substantially the same application of surface treatment 122 may be applied to witness coupon 118 and first surface 148. For example, if first surface 148 has scarf 130 of the same slope as scarf 134 of witness coupon 118, application of contamination 158 to witness coupon 118 and first surface 148 would be of about the same thickness.

Witness coupon 118 may provide added inspection functionality. In some exemplary embodiments, witness coupon 118 and first surface 148 of first material 126 may receive substantially the same application of surface treatment 122. In these exemplary embodiments, inspection of surface treatment 122 applied to witness coupon 118 may replace or supplement inspection of first surface 148 of first material 126 to identify characteristics of surface treatment 122.

Inspection of witness coupon 118 may reduce time needed for inspection instead of or in addition to inspection of first surface 148 of first material 126. After application of surface treatment 122, witness coupon 118 may be inspected while first material 126 receives further processing. As a result, processing of first material 126 may not be delayed for inspection.

Additionally, inspection of an independent witness coupon 118 may allow for indirect inspection of materials that may be more difficult to inspect than desired. In one illustrative example, first material 126 may be comprised of composite 142. Optical inspection of composite materials is often more difficult than desired, or may be ineffective. In one illustrative example, witness coupon 118 may be comprised of metal 170.

In one illustrative example, it may be easier or more effective to perform optical inspection of metal 170 that may be polished rather than perform optical inspection of a composite material. Further, witness coupon 118 does not need to be inspected immediately after application of surface treatment 122. In some illustrative embodiments, witness coupon 118 may be stored for later inspection. For example, witness coupon 118 may be inspected a day after application of surface treatment 122, a week after application of surface treatment 122, a month after application of surface treatment 122, or any other suitable time after application of surface treatment 122. Accordingly, characteristics of surface treatment 122 may be identified even after test specimen assembly 102 is formed.

Computer system 106 is configured to communicate with test specimen assembly generation system 104. As depicted, computer system 106 comprises database 176 and management software 178. Computer system 106 may control manufacturing of test specimen assembly 102 through management software 178. Database 176 may contain at least one of parameter of surface treatment equipment 110, inspection results, and levels of strength resulting from surface treatment 122.

The illustration of manufacturing environment 100 in FIG. 1 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, if first material 126 and second material 128 are pre-fabricated, manufacturing environment 100 may not contain composite layup equipment 114. As a further example, if no materials have a scarf, or if all scarfs are formed through composite layup, scarfing equipment 112 may not be present in manufacturing environment 100.

The integrity of an adhesive bond between two FRP laminates depends on strong chemical bonding and mechanical factors. Surface preparation can remove contamination and create a chemically active surface. Sanding, grit blasting, peel-ply removal and energetic surface preparation are known methods for preparing a FRP surface for adhesive bonding with another FRP surface.

The characteristics of the adherend are critical to the integrity of an adhesive bond. Because adhesion is a function of the chemical and physical nature of the surface, the properties of that surface will often govern the performance of a bonded joint. Surface characteristics that affect performance include: (1) surface roughness; (2) surface energy; (3) cleanliness/removal of contamination; and (4) chemical activity/functionality.

Various methods for repeatable surface preparation that can be used to manufacture weak bond standards having weak bond strengths not detectable by standard NDI techniques will now be described. The repeatable surface preparation techniques disclosed herein vary the activation of one of the surfaces to be bonded. The methods of manufacture disclosed herein can be used in any thickness of bond configuration based on the FRP thickness that it is applied to. Bonds created by these methods are indistinguishable in standard NDI examinations.

More specifically, some of the methods disclosed herein for fabricating a test specimen assembly comprise preparing the bonding surface of a first FRP adherend so that different areas on that bonding surface have different bonded joint performance-governing characteristics. A second FRP adherend having a uniform bonded joint performance-governing characteristic is then adhesively bonded to the first adherend, resulting in a test specimen assembly having a bonded joint with respective areas that have different adhesive bond strengths. This test specimen assembly is suitable for use as a standard when validating that a bond strength measurement system can in fact correctly detect a weak bond.

Figure 2:
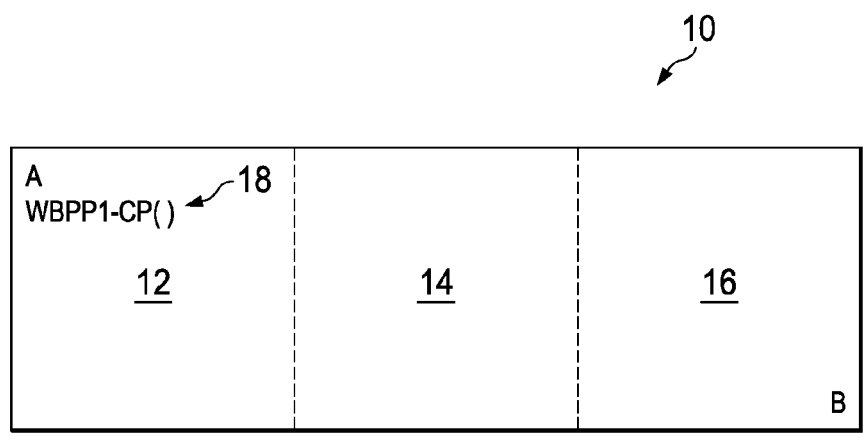
FIG. 2 is a drawing showing a plain view of a weak adhesive bond test specimen assembly in accordance with various illustrative embodiments.

The structure of an exemplary FRP test specimen assembly or standard 10 is shown in FIG. 2. In this example, the bonded joint of the FRP standard 10 has three areas 12, 14 and 16 in which the respective adhesive bond strengths differ from each other to a substantial degree. Each standard 10 is provided with an identifying label 18, e.g., WBPP1-CP1 through WBPP1-CP12 in the case wherein a precursor test specimen assembly was sectioned into 12 coupons or standards. The designations A and B seen in FIG. 2 indicate the orientation of the standard.

Figure 3:
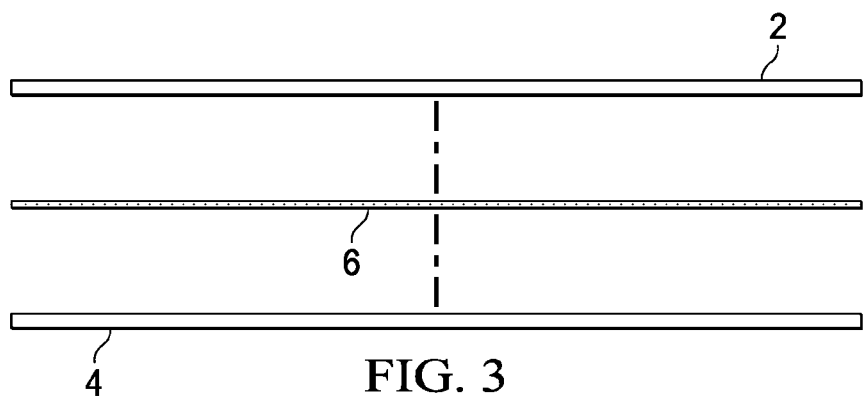
FIG. 3 is a drawing showing an exploded side view of the weak adhesive bond test specimen assembly depicted in FIG. 2.

As shown in FIG. 3, each test standard disclosed herein comprises first and second FRP laminates 2 and 4 that will be bonded together by adhesive 6. These components are depicted in the exploded view of FIG. 3 as being separated, but it should be appreciated that in the final assembled state the laminates 2 and 4 will both be in contact with and bonded by the cured adhesive 6 therebetween.

In accordance with the embodiments disclosed hereinafter, respective areas of a bonding surface of a FRP adherend (corresponding to the areas 12, 14 and 16 depicted in FIG. 2) may be treated using peel plies, plasma jets or laser beams.

Peel Ply-Based Adhesion for FRP-to-FRP Bonds

In accordance with some embodiments, the manufactured standard has variable bond strengths due to the use of different peel plies in the assembly. The method of manufacture uses a consistent product in the form of peel ply materials that are applied to the FRPs during the fabrication. Each peel ply type will result in a consistent surface type for bonding that will have different bond strength when assembled with the prescribed adhesive method.

A peel ply is a woven fabric that may be applied as the first or last layer on a FRP prepreg assembly before the part is cured. During cure, the epoxy in the first FRP part becomes viscous and flows into gaps in the peel ply. The peel ply is removed from the surface of the first FRP part immediately before the latter is adhesively bonded to a second FRP part. Because the peel ply does not bond to the first FRP part, it can be readily peeled off, leaving a surface texture on the first FRP part which is suitable for adhesive bonding to the surface of the second FRP part. The removal of the peel ply leaves a roughened surface on the first FRP part that does not require further processing (e.g., sanding or grit blasting) before laminating or bonding to the second FRP part.

Peel ply is used in the fabrication of FRP parts to protect a surface during handling and as a surface preparation method for a future bonding process. The peel ply comes in a variety of types from each manufacturer. Peel ply is normally a fabric layer that may be made from materials such as fiberglass, Kevlar, nylon or polyester. The peel ply is placed as the first ply on a tool surface and then the FRP layup is assembled. Following cure, the FRP part will be transported for a further assembly operation. At the time of the further assembly, the peel ply layer will be removed leaving a fresh surface for bonding. The peel ply removal is performed just prior to the bonding operation. The surface that is available for bonding will have a chemistry and texture that is a function of the peel ply used. Based on the peel ply type and the adhesive, variable strength will be found in the adhesive bond.

During the evaluation of adhesive bonding surface preparation methods, several types of peel ply have been investigated. The results of that study found that the peel ply could be used to develop controlled bond strength in a consistent, repeatable manner. Table 1 in the Appendix lists the peel ply types (manufactured by Precision Fabrics Group Inc.) that have been found to represent variable peel ply strength when used with AF 555 adhesive and BMS Toray FL96736-37K Type 40, Class 2, Style 6K-70-PW, Form 1 FRP material (manufactured by Toray Industries Inc.) using 350° F. curing.

Technical descriptions of the selected peel ply materials (all manufactured by Precision Fabrics Group) are as follows:
Polyester Peel Ply Fabric:
Code 60001
Style: 56009
Fiber: 100% polyester
Finish: Fin 060 NAT, Scoured and Heat Set
Finished Count (ASTM D 3775): 70 ends/inch Warp; 50 picks/inch FILL
Nylon Peel Ply Fabric:
Code 51789
Style: 52006
Fiber: 100% nylon 6, 6
Finish: Fin 060 NAT, Scoured and Heat Set Finished Count (ASTM D 3775): 160 ends/inch Warp; 103 picks/inch FILL
Nylon Peel Ply Fabric with Silicon Release Additive:
Code 51789
Style: 52006
Fiber: 100% nylon 6, 6
Finish: Fin 061 SRB, Super release Blue—an inert, heat-stabilized cross-linked polymer finish
Finished Count (ASTM D 3775): 160 ends/inch Warp; 103 picks/inch FILL As used herein, the term "AF 555 adhesive" refers to 3M™ Scotch-Weld™ Structural Adhesive Film AF 555. AF 555 adhesive is a 350° F. curing film designed for metal and FRP bonding in conjunction with honeycomb (sandwich construction) or in a laminate structure. This film can also be utilized for FRP surfacing. AF 555 film can be co-cured, co-bonded with FRP pre-pregs, or used to bond cured FRP.

FRP-to-FRP Peel Ply-Based Bond Standard

In accordance with one specific embodiment, the standard is constructed using three different peel plies in each of three regions of one of the adherends to be adhesively bonded. When the other adherend is assembled to the adherend that was prepared with three different peel plies after removal of the latter, the resulting adhesive bond will have zones of three different bond strengths. The adhesive bond strengths will be consistent whenever the process is repeated because of the consistency of the peel ply materials.

The aforementioned specific embodiment used nylon 6,6 SRB, nylon 6,6 and polyester peel plies (as described in Table 1) applied to one surface of a first laminate made of Toray FL96736-37K Type 40, Class 2, Style 6K-70-PW, Form 1 FRP material, while a single polyester peel ply was applied to one surface of a second laminate also made of Toray FL96736-37K Type 40, Class 2, Style 6K-70-PW, Form 1 FRP material. The different peel plies were removed from both laminates just prior to bonding. Then AF 555 film adhesive was applied to either or both peel ply-treated surfaces.

It should be noted that the peel ply materials selected for use will depend on the particular FRP material that the test specimens are made of. For example, Toray FL96736-37K Type 40, Class 2, Style 6K-70-PW, Form 1 FRP is compatible with polyester peel ply (i.e., produces a surface suitable for bonding), while the Cytec CYCOM 950/PWC T300 FRP is not compatible with polyester peel ply.

Standards having a structure conforming to FIGS. 2 and 3 were assembled using this peel ply technology. Each standard was 18 inches long by 6 inches wide, resulting in a bonded joint having three zones (areas 12, 14 and 16 in FIG. 2) of 6×6 inches with respective different adhesive bond strengths.

The weak bond standards based on variable peel ply selection consisted of 16-ply graphite epoxy FRP material bonded to 20-ply graphite epoxy FRP material by a hot film bonding process using AF 555 adhesive with 350° F. curing. The three different types of peel ply identified in Table 1 (see Appendix) were used during the manufacturing process on one of the adherends. More specifically, three equal-size areas of one surface of the 16-ply graphite epoxy FRP material were respectively covered with the peel plies identified in Table 1 prior to curing of the FRP material.

Similarly, an entire surface of the 20-ply graphite epoxy FRP material was covered with polyester peel ply BMS 8-308 prior to curing. After curing both FRP materials, the peel plies were removed, leaving consistent surface chemistry within each respective area of the 16-ply FRP laminate. AF 555 adhesive was then applied on one or both of the treated surfaces of the two FRP laminates and the laminates were pressed together with the adhesive therebetween. The adhesive was then cured at 350° F. The resulting bonded joint has three areas 12, 14 and 16 (see FIG. 2) with different adhesive bond strengths. In 2009 twelve standards were constructed and labeled WBPP1-CP1 through WBPP1-CP12.

Tables 2 and 3 (see Appendix) show the through transmission ultrasound (TTU) inspection scans of the twelve standards WBPP1-CP1 through WBPP1-CP12. The TTU signals do not indicate any differences between the respective peel ply regions. Tables 4 and 5 (see Appendix) are the pulse echo (PE) ultrasound inspection images of the same 12 standards. The PE results show bondline features due to the assembly, but no indications that identify a consistent change that could be correlated with the weak bond peel ply zones relative to the strong bond. The values shown are a ratio of the bondline signal to the front face signal. These data were taken from the 16-ply side of the samples. Similar images were obtained from the 20-ply side. The ultrasound inspection images showed no significant difference between the respective adhesive bond zones of the standards, providing no clue as to the strength in the various zones. Other NDI tests on the standards were also unable to distinguish a difference between the weak and strong bonded areas.

Weak Bond Standard Adhesive Strengths

Figure 4:
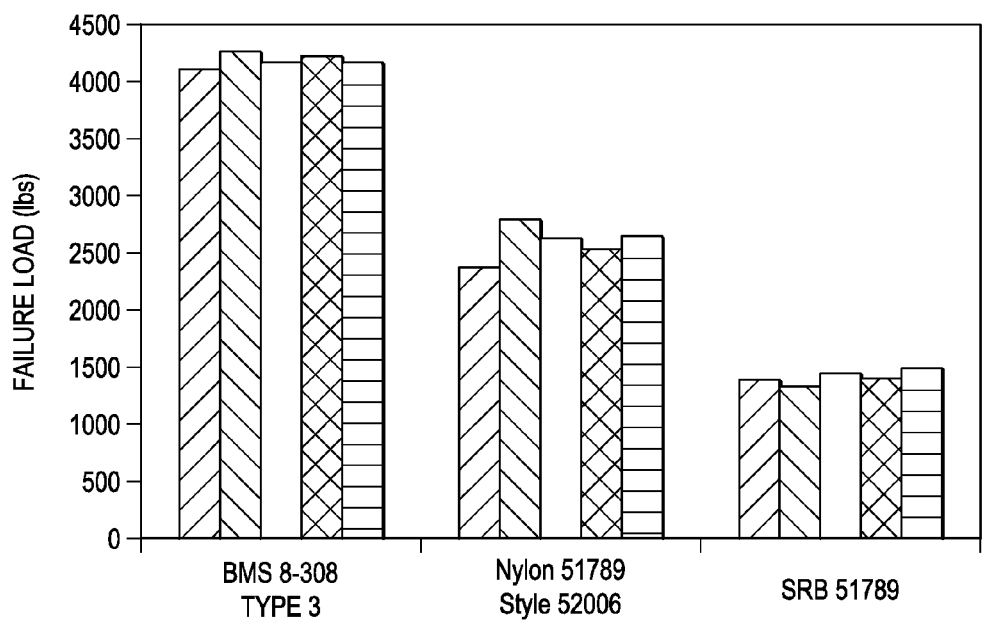
FIG. 4 is a bar chart showing lap shear failure loads for five weak bond test standards fabricated using the same set of three different peel ply materials.

The variable strength of the adhesive bonding using the peel ply surface preparation method from lap shear tests performed on five weak bond standards are shown in FIG. 4. Table 6 (see Appendix) summarizes the results of mechanical testing, i.e., lap shear, double cantilever beam (DCB) and flat-wise tension tests. The DCB and lap shear tests are baseline mechanical tests that demonstrate the success of the standard fabrication for creating variable adhesive bond strength. The lap shear tests were conducted in accordance with ASTM Standard D 3163-01; the Mode 1 interlaminar fracture toughness tests using DCB specimens were conducted in accordance with ASTM Standard D 5528-01. The flat-wise tension test was performed by using a trepanning method and bonding on an attachment. A tensile test load was applied by the DeFelsco adhesive bond tester. The trepanning flat-wise tension method involved drilling an annulus in one laminate to the bondline (leaving a center core of FRP material), fastening a plug to the center core of FRP material, and then applying tension on the plug until the center core of FRP material delaminated.

Weak Bond Standard Evaluation Methods

Nondestructive inspection has not been shown to be effective for finding weak bonds due to surface chemistry effects because there are no significant features to be detected at the interface. Nondestructive inspection operates in the elastic regime of materials, while strength is assessed in the plastic regime. Nondestructive inspection can detect weak bonds when the degradation of the bonds is due to feature changes that can be seen on NDI results. The weak bonds created by the peel ply method described above were shown to be undetectable by conventional ultrasonic NDI, which would be the standard inspection for a FRP-to-FRP bonded assembly.

Alternative methods that can be applied to bonds for testing are methods that stress the bond looking for deviation from standard response. Two methods tested were acoustic emission and laser bond inspection.

Figure 5:
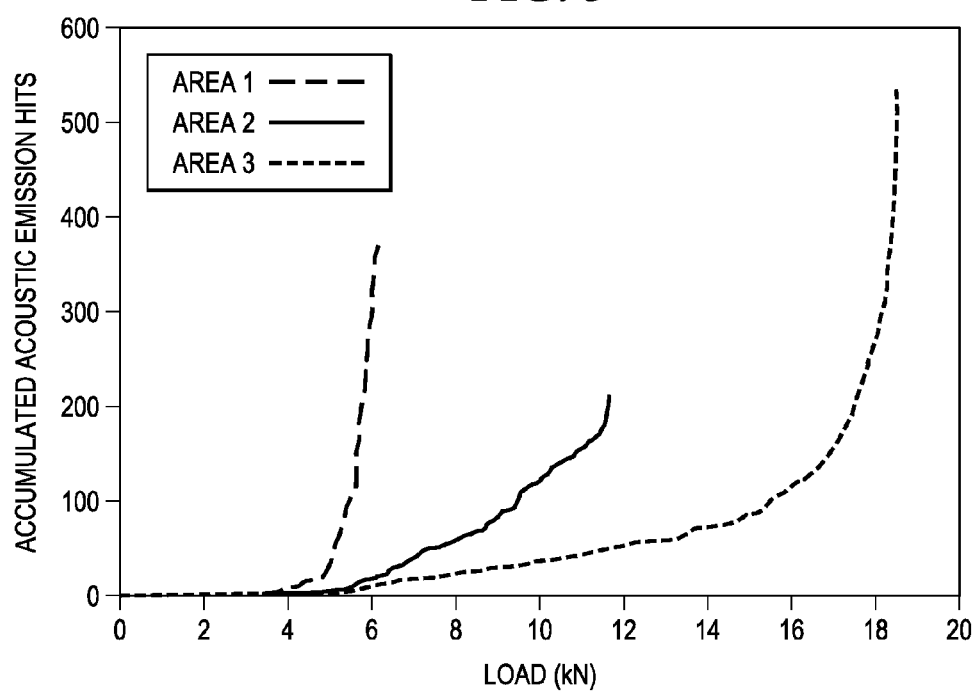
FIG. 5 is a graph showing accumulated acoustic emission hits versus load applied during lap shear testing for three areas of a weak bond test specimen assembly fabricated using three different peel ply materials.

The acoustic emission test was performed during lap shear testing. FIG. 5 shows the accumulated hits versus load (kN) for three adhesively bonded areas of a FRP test specimen assembly manufactured using peel plies as described above. Weaker bonds naturally create more hits as they approach failure. However for adequate testing, the loading would need to be relatively high, approaching 60% of the limit.

The laser bond inspection method uses high-intensity stress waves to create a tensile load at the bond interface. A detailed description of this method can be found in R. Bossi et al., "Laser Bonding Testing," *Materials Evaluation*, Vol. 67, No. 7, July 2009, pp. 819-827. Work was performed with the LBID system at LSP Technologies, Inc. in Dublin, Ohio. This system utilized a suitable Nd:glass laser (1054 nm wavelength). The laser produced 45 Joules/pulse with very high reproducibility. The laser was tailored to provide Gaussian-like pulse widths of 70 to 300 nsec.

Figure 6:
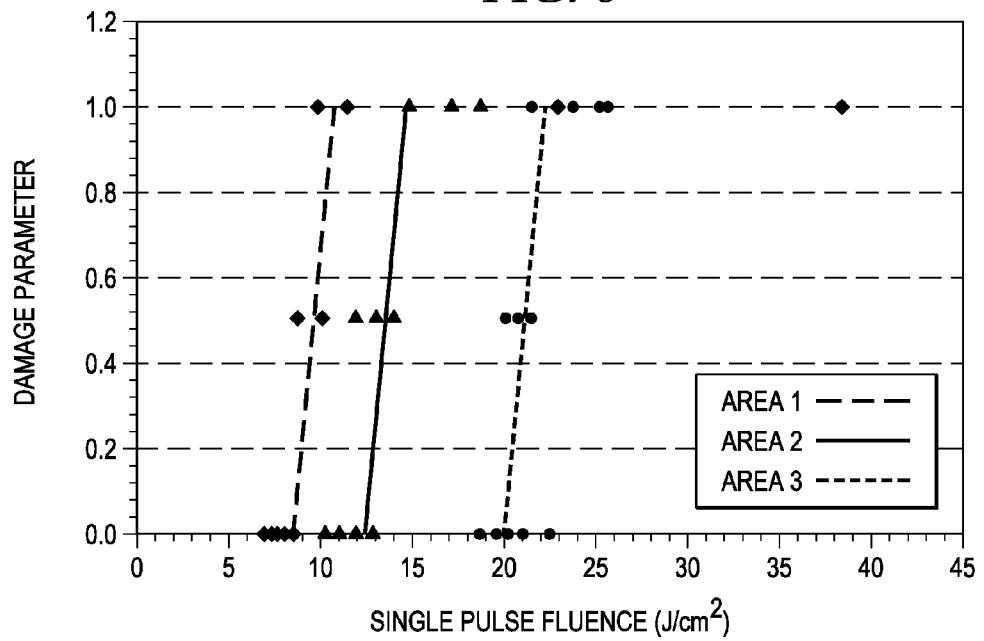
FIG. 6 is a plot of damage parameter versus laser fluence showing test results derived using a laser bond inspection method for three areas of a weak bond test specimen assembly fabricated using three different peel ply materials. The damage parameter varies from 0 (no damage) to 1 (debonded).

The weak peel ply bond standard was successfully tested using the laser bond inspection method. Table 7 (see Appendix) shows a summary of the laser bond inspection results. The relative power levels at which the SRB and nylon peel ply-treated surfaces fail relative to the polyester surface-treated baseline material are at 40% and 65% respectively. FIG. 6 shows a plot of the laser bond inspection test results over the three zones of the peel ply weak bond standard. The horizontal axis is the laser fluence. The vertical axis is a scale representing whether the bond failed or not, where 0 is no failure and 1 is clear failure. With increasing laser power, the weaker bond (Area 1) failed first; then the middle-strength bond (Area 2) failed; and then finally the full-strength bond (Area 3) failed. These data indicate that the laser bond inspection test is able to discriminate the weak bond standards fairly well.

Associated Peel Ply Weak Bond Creation

The weak bond standards described above were created using standard off-the-shelf peel ply material. These can be repeatedly obtained and used for the construction. It is also possible to construct weak adhesion surfaces from peel ply material by modifying an existing peel ply material. In this case the peel ply material is allowed to soak in a solution of release agent material for a controlled time and then removed and dried. When differing concentrations or times are used for the bath, variable bond strengths may be obtained from the peel ply application in a bonding test.

In accordance with some embodiments, a commercially available peel ply material (e.g., a polyester peel ply material that had been scoured only and not heat set) can be soaked for a controlled time in a concentrated bath containing a release agent material (e.g., siloxane). By controlling the concentration and time, variable levels of peel ply contamination can be achieved. [The term "scouring" refers to an operation that is similar to a large washing machine that uses caustic chemicals. Its purpose is to remove any contaminants, such as oils and sizings, from all surfaces of the cloth. These contaminants may be put on the fabric to facilitate the previous weaving operations.]

In one study reported by P. Van Voast et al. in "Effect of Varying Levels of Peel Ply Contamination on Adhesion Threshold," SAMPE 2010, May 17-20, Seattle, Wash. (the contents of which are incorporated by reference herein in their entirety), polyester peel ply material was contaminated with mixes containing the following amounts of siloxane: 0% (deionized water), 0.0001%, 0.001%, 0.01%, 0.05%, 0.1%, 0.2%, 0.3%, 0.4%, 0.5%, 1% and 2%. The solutions were applied to fabric samples using a laboratory scale Werner Mathis AG textile padder and dried and heat set in a laboratory scale Werner Mathis AG tenter frame. The pressure at the pad was 400 kPa and the pad speed was 2.4 meters per minute. The contaminated samples were dried for 65 seconds at 188° C.

Figure 10:
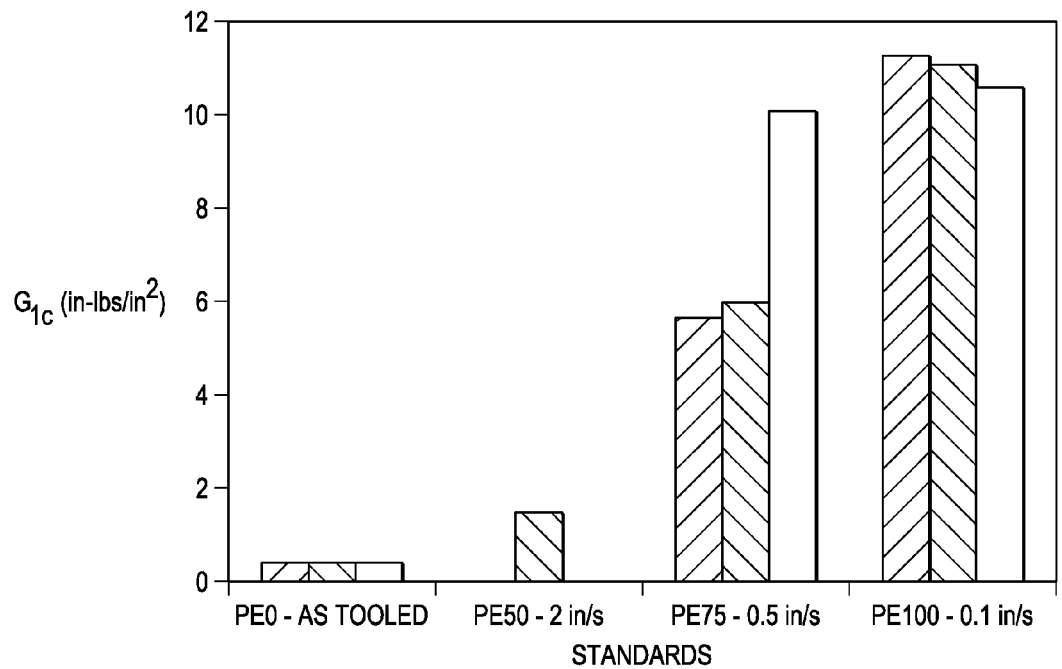

The FRP laminates used for this study were produced from 180° C. (350° F.) curing of carbon fiber-reinforced epoxy prepreg (Toray 3900-2/T800 Grade 190 tape). Polyester peel ply (Precision Fabric Group Style 60001) with a prescribed level of contamination was applied to the tool side of the laminate adherend. All laminate adherends were cured with a 2.8° C. (5° F.) per minute heat-up rate to 179° C. (355° F.) and allowed to dwell for 2 hours. The autoclave pressure was 0.58 MPa (85 psi) and full vacuum (29 mm Hg), which was maintained during the cure cycle. Bonding of the laminates was accomplished by removing the peel ply and applying one of four film adhesives. The adhesives evaluated were: 3M AF 555, Cytec Engineered Materials MB1515-3, Henkel EA9657 and PL795. Bond assemblies were cured with the same cure cycle as the laminates, except the pressure was reduced to 0.30 MPa (45 psi). Several adhesion tests were evaluated to determine their relative efficacy and adhesion threshold. Test results showed that the siloxane contamination had no measurable effect on adhesion until a threshold level of 1% siloxane contamination was reached. In particular, the DCB test results (see FIG. 10 in the Van Voast et al. article cited above) showed that the peel strength of the bonded assemblies decreased by at least 40% when the siloxane concentration was increased from 1% to 2%.

The calculated solids of siloxane is a more accurate method of discussing the level of contamination. The 2% contamination level corresponds to 4923 ppm siloxane in the mix. The levels of siloxane expected to be most useful for producing incremental weak bonds are in the range of 1000 to 6000 ppm calculated siloxane solids.

In order to manufacture test specimen assemblies using peel ply having varying levels of contamination, tests can be performed to find those contamination levels which produce in respective areas adhesive bond strengths reduced by respective percentages. For example, a test specimen assembly of the type depicted in FIG. 2 can be fabricated in which areas 12, 14 and 16, having respective different adhesive bond strengths, are produced using peel ply material having different levels of contamination. For example, the corresponding areas on the surface of a first FRP test specimen could be treated with peel ply material subjected to three different levels of contamination, while the surface of a second FRP test specimen (to be adhesively bonded to the first FRP test specimen to form a test specimen assembly) is treated with one peel ply material uniformly across all three areas. For example, the peel ply material having different levels of contamination can be produced by applying solutions containing different concentrations of siloxane.

Energetic Surface Preparations

Further illustrative embodiments rely on energetic surface preparation. The energetic surface preparation techniques disclosed below create a consistent bond that has controlled strength value based on the process. In addition, the zones of weakened strength in the test specimen assembly (i.e., bonded standard) may be of variable size and shape with no detectable physical edges. Further, the variable strength is not detectable by features that can be detected by conventional NDI methods. The energetic method uses plasma or laser surface etching that is robotically controlled to produce variable surface conditions on FRP adherends. The robotic controller is a processor programmed for easy repetition and easy variation of the level of surface modification and of the shape of the treated zone. Bonds created by these methods will appear consistent over the entire standard by conventional NDI examinations.

The preferred energetic surface preparation techniques use either a plasma or laser etching process to modify the surface of a FRP adherend. These two processes are described in the next sections. The development of weak bond standards in the following discussion of energetic surface preparation discussion is for FRP-to-FRP joints.

Plasma Etch Surface Preparation

Plasma etching is a surface treatment method that uses gases in a plasma state of ions, electrons and excited species. The interaction of the plasma gas with the surface of a polymer will result in surface modification. The interaction occurs in the first few atomic layers, causing bonds to break and creating an energized surface. The bulk property of the polymer is not affected. The surface, however, is activated, increasing the wettability and improving bonding. Gases can be specific, such as noble gases, oxygen or nitrogen, but even air plasma is acceptable.

In accordance with one surface treatment method, a surface of a FRP substrate was exposed to a plasma jet generated by an atmospheric (i.e., open-air) plasma generator. The plasma generator used was Model FG1001 with a flume (rotation jet) head model No. RD1004 commercially available from Plasmatreat North America, Inc. This plasma generator was operated with the following parameters: Power—140 volts and 8.5-9.0 amperes; Air Pressure—45 psi; Flume Head Rotation—On. The plasma generator was mounted on a robotic arm. Robotic arm and platen model No. I&J2400 (industrial robot), commercially available from Fisnar Inc. Wayne, N.J., was used.

The atmospheric plasma generator uses compressed air to make a nitrogen-oxygen plasma. A vacuum chamber or shielded environment is not needed. Plasma units can use compressed air as the standard gas input, or can employ other gas inputs to achieve specific surface properties. The plasma oxidizes contaminants from the treated surface and can be used to alter the surface chemistry by reacting ions and free radicals in the plasma with that surface. The Plasmatreat Model FG1001 plasma generator with flume head model No. RD1004 produces a plasma flume that can be rotated to create a plasma ring.

The plasma flume was raster scanned over the FRP surface using the robotic arm. Variables that were controlled during the process included the flume head height, rastering speed and flume rotation. Head height is the distance from the tip of the flume head to the FRP surface. Rastering speed is how fast the flume head travels over the FRP surface. Flume rotation is specific to the flume jet used. The plasma flume can be used as a single jet or the flume can be rotated, creating a ring of plasma with a diameter of approximately 20 mm. This spreads the flume out so a larger surface area can be treated and lessens the effect of overlap when raster scanning in an x-y coordinate system. All tests were conducted with the flume rotation on and with a 50% overlap in the rastering pattern.

Figure 7:
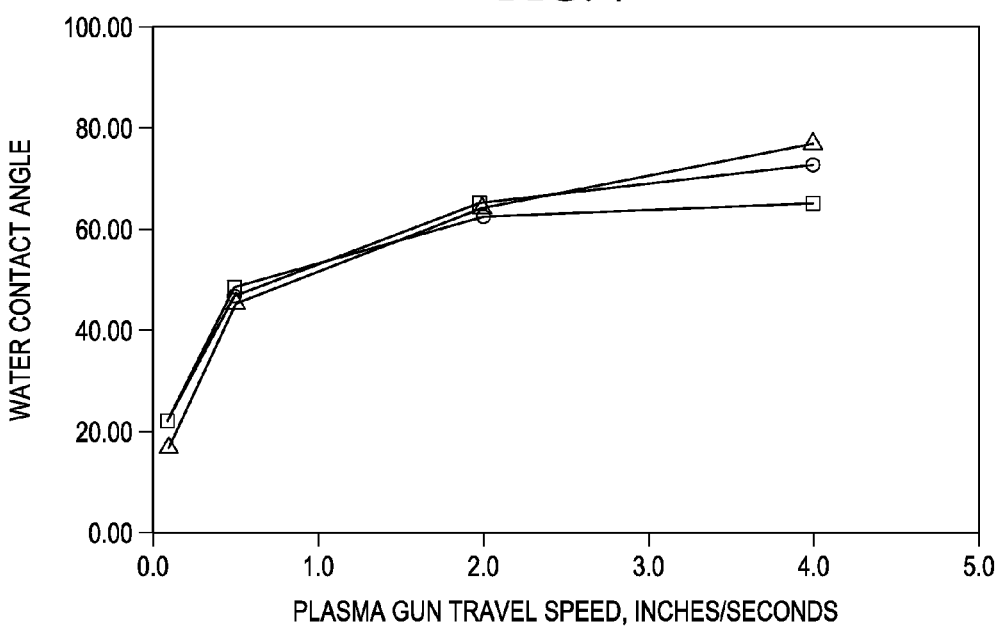
FIG. 7 is a plot showing water contact angle measurements at three time intervals after activation (■: 1 hr; ●: 5 hr; Δ: 24 hr) as a function of the travel speed (inches/sec) of a plasma gun following plasma treatment at a gun height of 0.50 inch.
Figure 8:
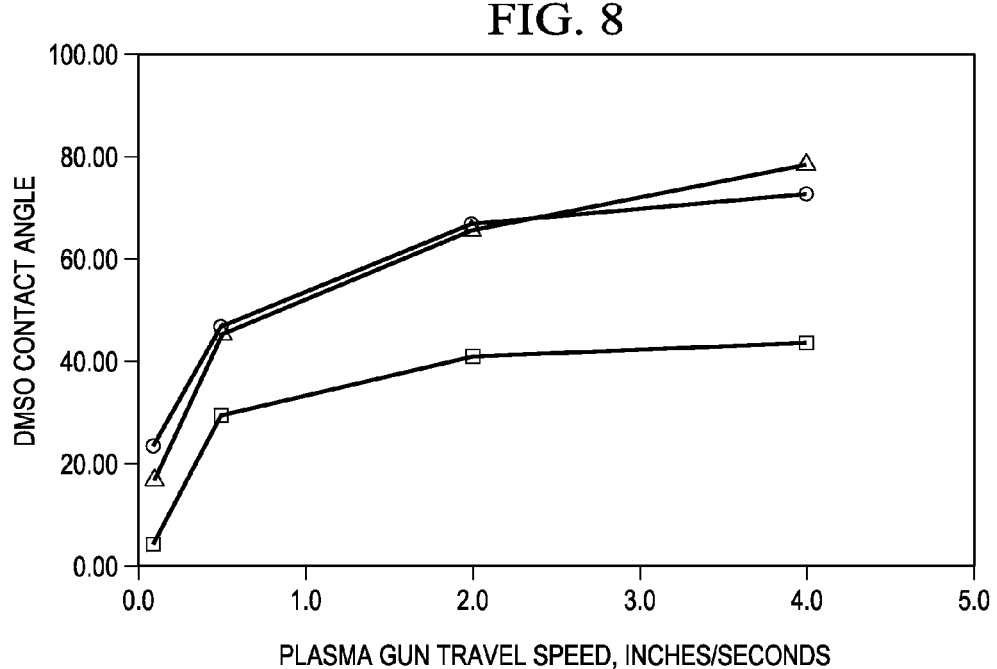
FIG. 8 is a plot showing DMSO contact angle measurements three time intervals after activation (■: 1 hr; ●: 5 hr; Δ: 24 hr) as a function of the travel speed (inches/sec) of a plasma gun following plasma treatment at a gun height of 0.50 inch.

To develop weak bond standards using plasma etching, a test was performed to measure the surface energy as a function of plasma etching parameters. FIGS. 7 and 8 respectively show the contact angle measurements for surface energy from water and dimethyl sulfoxide (DMSO) taken on the surface of a treated panel. The surface was FRP fabric of Toray FL96736-37K Type 40, Class 2, Style 6K-70-PW, Form 1. The graphs plot the contact angle versus the travel speed of the plasma treater. The head height to the surface was 0.5 inch. Other head heights were tested with 0.5 inch being selected based on the range of values in the contact angle curves. The results for DMSO contact angle show a shift of the surface energy between 1 and 5 hours that is not seen with the water contact angle. Based on these curves, significant changes in wettability should take place for plasma head travel speeds between 0.1 and 2 inches/sec when used at a 0.5-inch head height above the object.

Based on the curves seen in FIGS. 7 and 8, plasma etching was performed to create double cantilever beam (DCB) test standards for determining bond strength as a function of plasma etching level. The surfaces of both DCB adherends were plasma etched using the same process parameters. Table 8 (see Appendix) shows the plasma etch levels selected for the testing of respective DCB samples. The activity of the plasma on a surface is controlled by the energy of the plasma source, the distance from the surface, and the travel speed over the surface. For this test, the plasma energy and distance from the substrate were held constant and the travel speed was varied. The DCB samples were made with 13-ply laminates that consisted of a first ply of Toray FL96736-37K Type 40, Class 2, Style 6K-70-PW, Form 1 FRP fabric, eleven (0 degree orientation) plies of Toray P2352W-19 Type 35, Class 10, Grade 190, Form 3 tape and then a last ply of the same fabric. The plasma-etched laminates were bonded together using Henkel EA9696, Grade 10 250° F.-curing epoxy adhesive.

Following bonding, the samples were inspected using Through Transmission Ultrasound (TTU) imaging of the post-cured samples. The TTU signal data in the bond region for the four samples were as follows: PE0—17.2±0.5 dB; PE50—17.3±0.9 dB; PE75—16.8±0.5 dB; PE100—16.9±0.5 dB. The data indicates that there were no significant differences between the samples with different levels of plasma etch surface preparation using a standard NDI technique.

Figure 9:
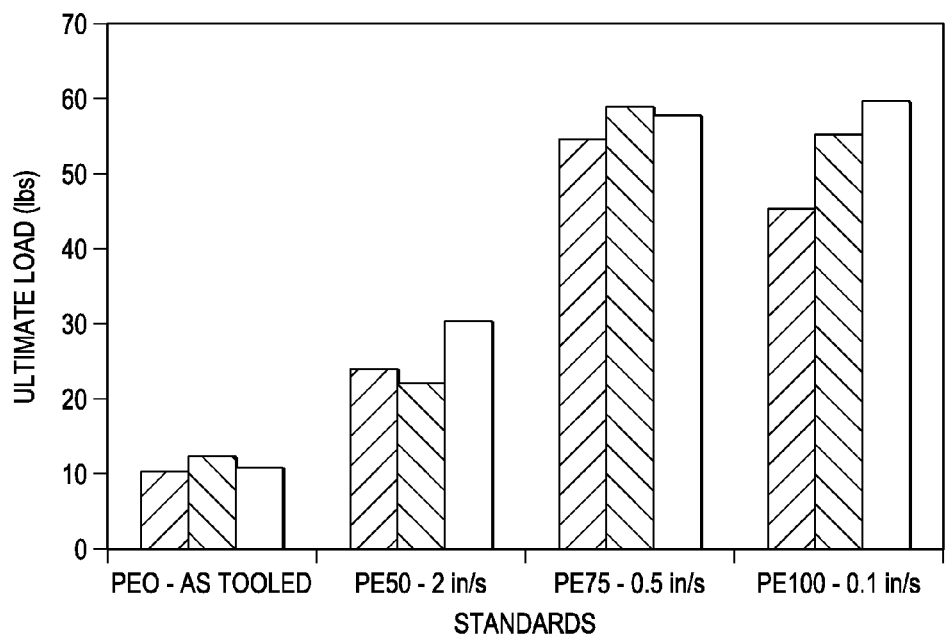
FIGS. 9 and 10 are respective bar charts showing ultimate loads and mode 1 crack strain energy release rates $G_{1c}$ for a plurality of test standards subjected to a double cantilever beam (DCB) test method, one set of three test standards being as tooled and the others having been treated by plasma etching at different plasma gun speeds.

Three DCB test standards were created from each bonded sample and testing was performed. The testing includes acoustic emission sensors. DCB testing measures the mode 1 crack strain energy release rate $G_{1c}$. The DCB ultimate load and $G_{1c}$ values are plotted in FIGS. 9 and 10 respectively. Table 9 (see Appendix) summarizes the values. In the case of the weak plasma etch (2 inches/sec), the $G_{1c}$ values could not be calculated accurately. A review of the surface failures indicated cohesive failure for the PE100, 0.1 inch/sec standards, a mixed cohesive interfacial failure for the PE75, 0.5 inch/sec standards and interfacial failure for the PE50, 2 inches/sec and PE0, as-tooled standards. Based on these tests, plasma etching can be a suitable source for creating controlled weak bonds in a FRP test specimen assembly.

In order to manufacture test specimen assemblies using plasma etching, tests can be performed to find those plasma etching parameters which respectively produce adhesive bond strengths reduced by respective percentages. For example, a test specimen assembly of the type depicted in FIG. 2 can be fabricated in which areas 12, 14 and 16, having respective different adhesive bond strengths, are produced using different plasma etching levels. For example, the corresponding areas on the surface of a first FRP test specimen could be subjected to three different plasma etching levels, while the surface of a second FRP test specimen (to be adhesively bonded to the first FRP test specimen to form a test specimen assembly) is subjected to uniform plasma etching across all three areas. The different plasma etching levels applied to the surface of the first FRP test specimen can be achieved by varying one or more of a plurality of plasma process parameters selected from the group comprising: travel speed of the plasma jet source, energy of the plasma jet source, and distance of the plasma jet source from the surface of the FRP test specimen.

Laser Etch Surface Preparation

Laser systems can be used to treat the surfaces of FRP substrates. The neodymium-doped yttrium aluminum garnet (Nd:YAG) laser is the most common laser in use and such lasers are commercially available in a variety of configurations and optical packages.

Laser surface preparation uses laser beam energy to affect the surface condition of the bond interface. The laser removes a thin film of resin from the FRP surface, leaving a pristine bonding surface similar to peel ply. It is highly dependent on the type of laser used and wavelength generated. The 1064 nm wavelength generated by most Nd:YAG lasers is absorbed by carbon fibers. This breaks apart the fiber and ablates the surface of the resin, leaving behind a weak crystalline structure unsuitable for bonding. Frequency doubling and tripling can be used to change the wavelength. An ideal treatment would utilize a wavelength that is absorbed by the resin and leaves the fibers undamaged. Factors such as power output of a pulsed laser beam source, pulse frequency of the pulsed laser beam, pulse repetition rate, diameter of the pulsed laser beam and step index of the laser beam spot can be varied depending on the laser system and optics chosen.

In a controlled study, laser processing was compared with the plasma etching and grit blasting methods. A frequency-tripled (1 watt) Nd:YAG laser was used to treat DCB adherends made of Toray FL96736-37K Type 40, Class 2, Style 6K-70-PW, Form 1 FRP material. The frequency-tripled wavelength of 355 nm is absorbed by the resin. The laser removed a thin film of resin, leaving behind a pristine bonding surface, similar to the effect of peel ply. It is also possible that there were changes in the surface chemistry of the resin. The laser was pulsed and the pulsed beam was raster scanned across the surface of the DCB adherends. The laser-etched DCB adherends were then bonded to form DCB specimens using EA9696 adhesive.

Figure 11:
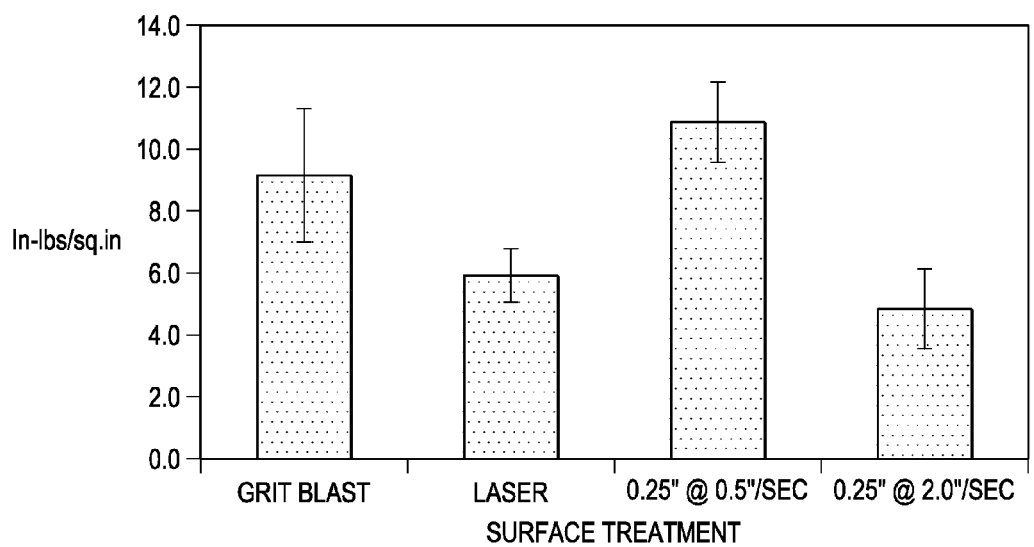
FIG. 11 is a bar chart showing mode 1 crack strain energy release rates $G_{1c}$ for a plurality of test standards subjected to a double cantilever beam (DCB) test method, the test standards being prepared using different surface preparation techniques, including grit blasting, laser etching and plasma etching at different travel speeds.

The DCB specimens prepared by laser etching were compared to specimens prepared by grit blasting and plasma etching. The $G_{IC}$ results are shown in Table 10 and FIG. 11. The laser preparation showed a weak bond that could similarly be obtained by grit blasting or plasma etching. Selection of variable laser power and dwell times could successfully create controlled weak bonds of variable strength.

In order to manufacture test specimen assemblies using laser etching, tests can be performed to find those laser etching parameters which respectively produce adhesive bond strengths reduced by respective percentages. For example, a test specimen assembly of the type depicted in FIG. 2 can be fabricated in which areas 12, 14 and 16, having respective different adhesive bond strengths, are produced using different laser etching levels. For example, the corresponding areas on the surface of a first FRP test specimen could be subjected to three different laser etching levels, while the surface of a second FRP test specimen (to be adhesively bonded to the first FRP test specimen to form a test specimen assembly) is subjected to uniform laser etching across all three areas. The different laser etching levels applied to the surface of the first FRP test specimen can be achieved by varying one or more of a plurality of laser process parameters selected from the group comprising: pulse frequency, power output, scanning speed and beam diameter.

Common Aspects of Disclosed Methods of Fabrication

The methods of fabricating test specimen assemblies disclosed above have the following aspects in common.

Figure 12:
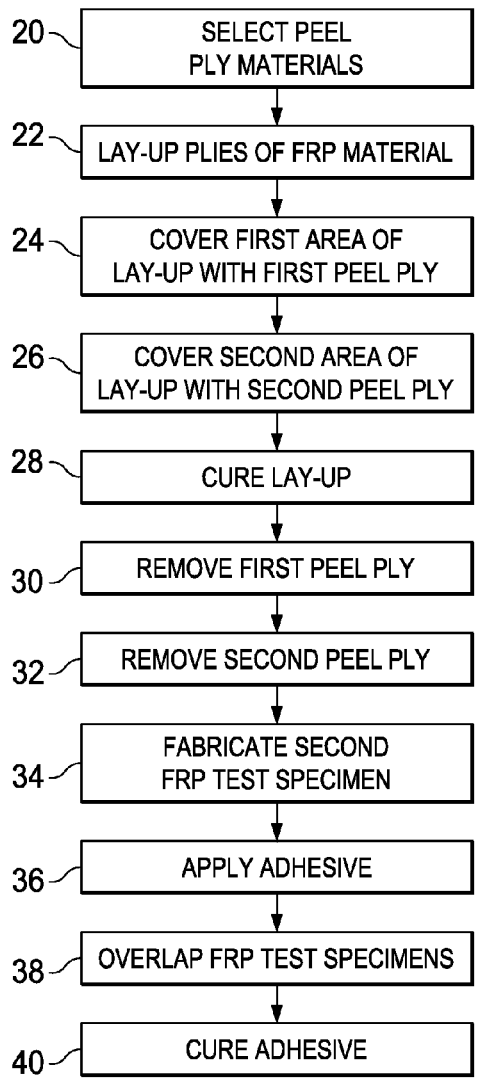
FIG. 12 is a flowchart showing common aspects of methods for repeatedly fabricating a test specimen assembly having controlled variable bond strengths using peel ply material.

First, as shown in FIG. 12, each disclosed method for repeatedly fabricating a test specimen assembly having controlled variable bond strengths using peel ply material comprises the following steps:

(a) selecting first and second peel ply materials, the first peel ply material being different than the second peel ply material (step 20 in FIG. 12);

(b) laying up a plurality of plies of fiber-reinforced plastic material (step 22);

(c) covering a first area of the lay-up with the first peel ply material (step 24);

(d) covering a second area of the lay-up with the second peel ply material, wherein the first and second areas do not overlap (step 26);

(e) curing the lay-up of fiber-reinforced plastic material with the first and second peel ply materials in place to form a first fiber-reinforced plastic test specimen (step 28);

(f) removing the first peel ply material to expose a first area of a bonding surface of the first fiber-reinforced plastic test specimen (step 30), the result being that the first area of the bonding surface of the first fiber-reinforced plastic test specimen has a first bonded joint performance-governing characteristic;

(g) removing the second peel ply material to expose a second area of the bonding surface of the first fiber-reinforced plastic test specimen (step 32), the result being that the second area of the bonding surface of the first fiber-reinforced plastic test specimen has a second bonded joint performance-governing characteristic different than the first bonded joint performance-governing characteristic;

(h) fabricating a second fiber-reinforced plastic test specimen having a bonding surface (step 34);

(i) applying adhesive on the bonding surface of one or both of the first and second fiber-reinforced plastic test specimens (step 36);

(j) placing the bonding surface of the first fiber-reinforced plastic test specimen in overlapping relationship with the bonding surface of the second fiber-reinforced plastic test specimen with the adhesive therebetween, the adhesive being in contact with the first and second areas of the bonding surface of the first fiber-reinforced plastic test specimen and with the bonding surface of the second fiber-reinforced plastic test specimen (step 38); and (k) curing the adhesive to bond the first and second fiber-reinforced plastic test specimens together (step 40).

Figure 13:
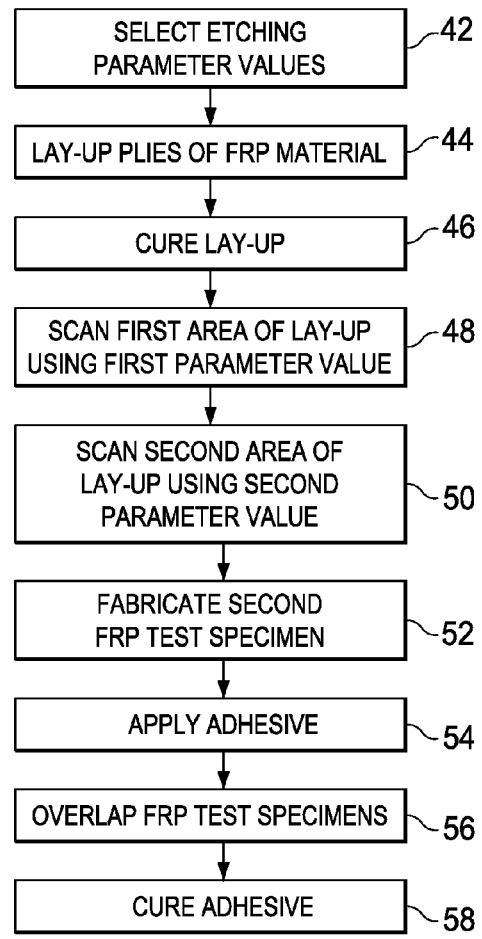
FIG. 13 is a flowchart showing common aspects of methods for repeatedly fabricating a test specimen assembly having controlled variable bond strengths using plasma or laser etching.

Second, as shown in FIG. 13, each disclosed method for repeatedly fabricating a test specimen assembly having controlled variable bond strengths using a plasma or laser etching process comprises the following steps:

(a) selecting first and second values of an etching process parameter, the first value being different than the second value (step 42 in FIG. 13);

(b) laying up a plurality of plies of fiber-reinforced plastic material (step 44);

(c) curing the lay-up of fiber-reinforced plastic material to form a first fiber-reinforced plastic test specimen having a bonding surface (step 46);

(d) moving a plasma jet or laser beam to scan over a first area of the bonding surface of the first fiber-reinforced plastic test specimen while the etching process parameter equals the first value (step 48), the result being that the first area of the bonding surface of the first fiber-reinforced plastic test specimen has a first bonded joint performance-governing characteristic;

(e) moving a plasma jet or laser beam to scan over a second area of the bonding surface of the first fiber-reinforced plastic test specimen while the etching process parameter equals the second value, wherein the first and second areas do not overlap (step 50), the result being that the second area of the bonding surface of the first fiber-reinforced plastic test specimen has a second bonded joint performance-governing characteristic different than the first bonded joint performance-governing characteristic;

(f) fabricating a second fiber-reinforced plastic test specimen having a bonding surface (step 52);

(g) applying adhesive on the bonding surface of one or both of the first and second fiber-reinforced plastic test specimens (step 54);

(h) placing the bonding surface of the first fiber-reinforced plastic test specimen in overlapping relationship with the bonding surface of the second fiber-reinforced plastic test specimen with the adhesive therebetween, the adhesive being in contact with the first and second areas of the bonding surface of the first fiber-reinforced plastic test specimen and with the bonding surface of the second fiber-reinforced plastic test specimen (step 56); and (i) curing the adhesive to bond the first and second fiber-reinforced plastic test specimens together (step 58).

Figure 14:
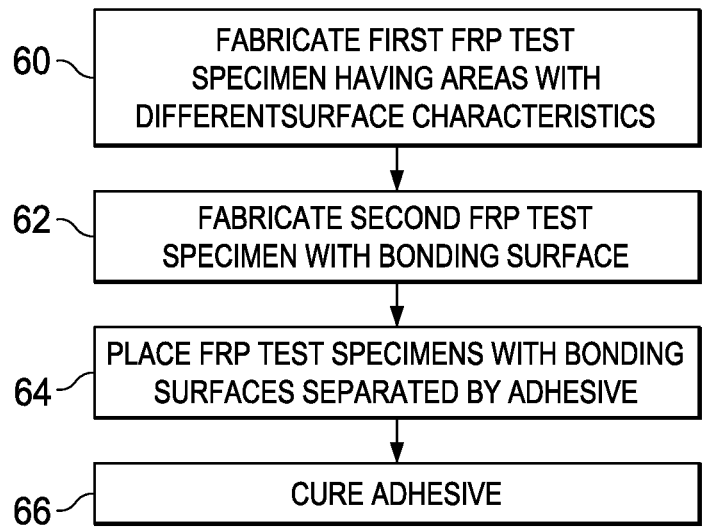
FIG. 14 is a flowchart showing common aspects of the fabrication methods depicted in FIGS. 12 and 13.

Moreover, as shown in FIG. 14, the common aspects of the fabrication methods depicted in FIGS. 12 and 13 comprise the following steps:

(a) fabricating a first fiber-reinforced plastic test specimen having a bonding surface, wherein a first area of the bonding surface of the first fiber-reinforced plastic test specimen has a first bonded joint performance-governing characteristic, while a second area of the bonding surface, not overlapping with the first area, of the first fiber-reinforced plastic test specimen has a second bonded joint performance-governing characteristic different than the first bonded joint performance-governing characteristic (step 60 in FIG. 14);

(b) fabricating a second fiber-reinforced plastic test specimen having a bonding surface (step 62);

(c) placing the bonding surface of the first fiber-reinforced plastic test specimen in overlapping relationship with the bonding surface of the second fiber-reinforced plastic test specimen with adhesive therebetween, the adhesive being in contact with the first and second areas of the bonding surface of the first fiber-reinforced plastic test specimen and with the bonding surface of the second fiber-reinforced plastic test specimen (step 64); and (d) curing the adhesive to bond the first and second fiber-reinforced plastic test specimens together (step 66).

Figure 15:
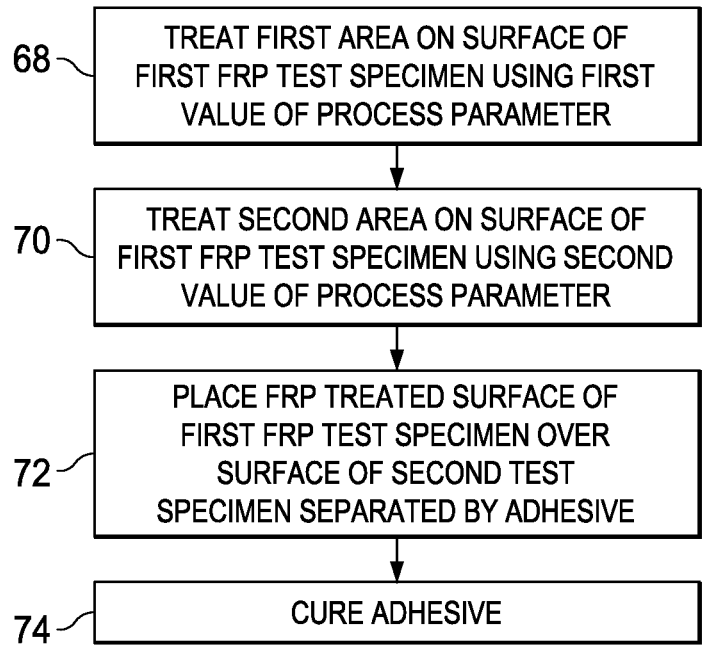
FIG. 15 is a flowchart showing the common aspects of the fabrication methods using plasma or laser etching wherein the common aspects are characterized more broadly than is done in FIG. 13.

Alternatively, as shown in FIG. 15, the common aspects of the above-disclosed fabrication methods using plasma or laser etching can be characterized more broadly as comprising the following steps:

(a) applying a first surface treatment process over a first area of a surface of a first fiber-reinforced plastic test specimen (step 68 in FIG. 15);

(b) applying a second surface treatment process over a second area of the surface of the first fiber-reinforced plastic test specimen, wherein each of the first and second surface treatment processes comprises a process parameter, the process parameter for the first surface treatment process being equal to a first value, and the process parameter for the second surface treatment process being equal to a second value that is different than the first value (step 70);

(c) placing the treated surface of the first fiber-reinforced plastic test specimen in overlapping relationship with a surface of a second fiber-reinforced plastic test specimen with adhesive therebetween, the adhesive being in contact with the first and second areas of the treated surface of the first fiber-reinforced plastic test specimen and with the surface of the second fiber-reinforced plastic test specimen (step 72); and (d) curing the adhesive to bond the first and second fiber-reinforced plastic test specimens together (step 74).

Figure 16:
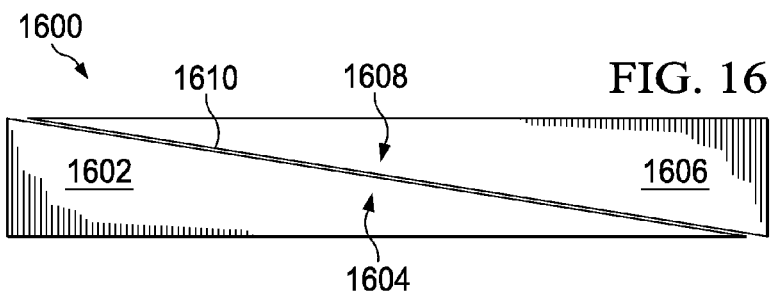
FIG. 16 is an illustration of a cross-sectional view of a test specimen assembly comprising a scarf surface in accordance with an illustrative embodiment.

Turning now to FIG. 16, an illustration of a cross-sectional view of a test specimen assembly comprising a scarf surface is depicted in accordance with an illustrative embodiment. Test specimen assembly 1600 is an example of a physical implementation of test specimen assembly 102 shown in block form in FIG. 1.

As depicted, first material 1602 has scarf 1604. Second material 1606 has scarf 1608. Scarf 1608 of second material 1606 and scarf 1604 of first material 1602 have substantially the same slope. Adhesive 1610 bonds scarf 1604 of first material 1602 and scarf 1608 of second material 1606.

As depicted, although scarf 1604 of first material 1602 and scarf 1608 of second material 1606 run the full length of test specimen assembly 1600, scarf 1604 and scarf 1608 do not need to extend the full length of test specimen assembly 1600. Scarf 1604 may comprise a portion of first material 1602. Likewise, scarf 1608 may comprise a portion of second material 1606. In such illustrative embodiments, scarf 1604 of first material 1602 or scarf 1608 of second material 1606 may extend only a portion of the length of test specimen assembly 1600.

Figure 17:
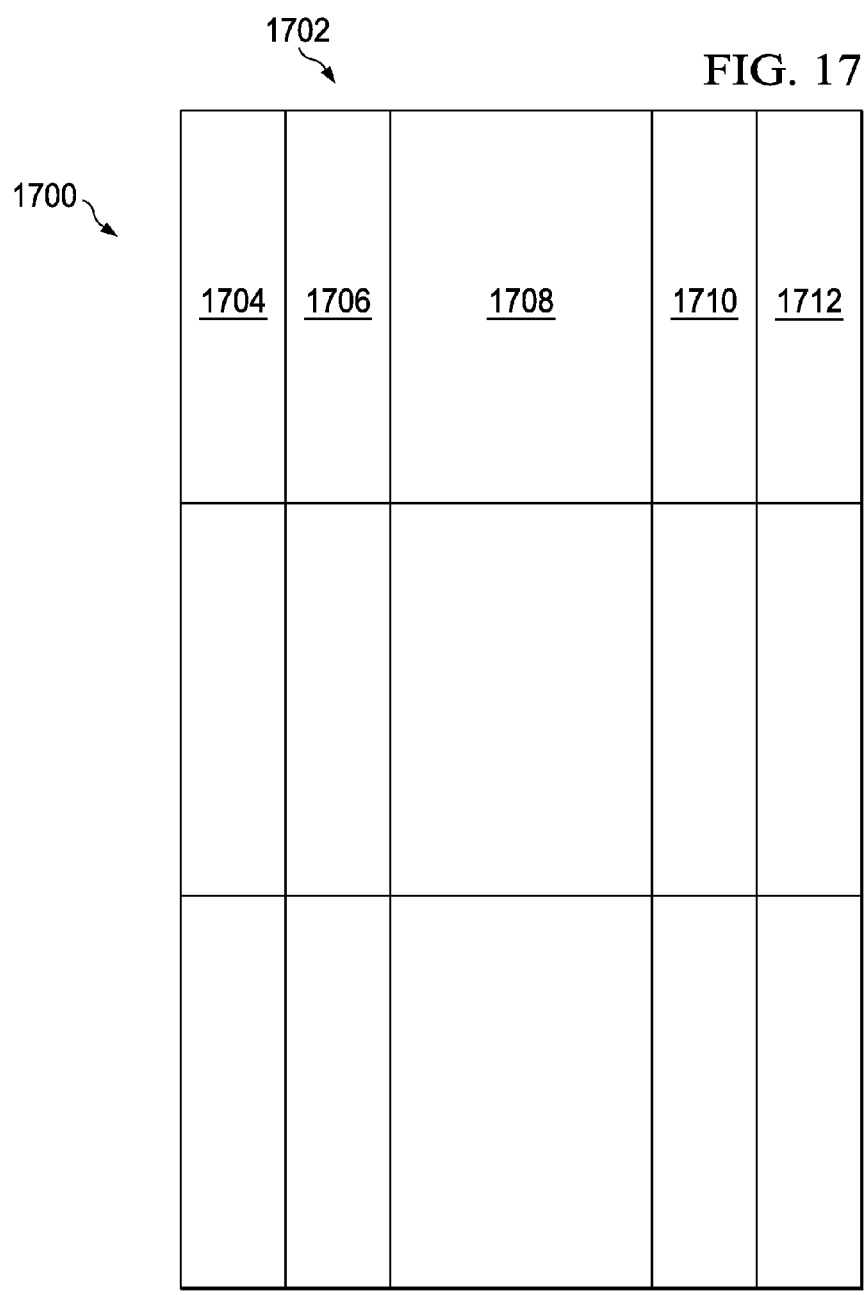
FIG. 17 is an illustration of a test specimen assembly with test specimen strips indicated in accordance with an illustrative embodiment.

With reference now to FIG. 17, an illustration of a test specimen assembly with test specimen strips indicated is depicted in accordance with an illustrative embodiment. As depicted test specimen assembly 1700 is an example of test specimen assembly 102 of FIG. 1.

Test specimen assembly 1700 may be separated into plurality of test specimen strips 1702. Test specimen assembly 1700 may be separated into plurality of test specimen strips 1702 by cutting, scoring, bending, or any other suitable method for separating test specimen assembly 1700. As depicted, plurality of test specimen strips 1702 in test specimen assembly 1700 comprises test specimen strip 1704, test specimen strip 1706, test specimen strip 1708, test specimen strip 1710, and test specimen strip 1712.

In one illustrative example, test specimen strip 1704, test specimen strip 1706, test specimen strip 1710, and test specimen strip 1712 have the same dimensions, while test specimen strip 1708 has different dimensions. As depicted, test specimen strip 1708 is larger than test specimen strip 1704, test specimen strip 1706, test specimen strip 1710, and test specimen strip 1712.

The larger size of test specimen strip 1708 may accommodate non-destructive inspection equipment which may require larger test specimen strips. Test specimen strip 1708 may be tested by inspection equipment prior to or following testing a bond. Testing of test specimen strip 1708 may determine whether the inspection equipment detects the strength of the bonds as accurate as desired. Testing of test specimen strip 1708 may be used in calibration of inspection equipment. Calibration may include identifying a setting of the inspection equipment for inspection of a bond below the desired strength. For example, testing of test specimen strip 1708 may be used to identify a power setting for laser bond inspection equipment.

Testing of test specimen strip 1708 may include loading of the bond in the testing. In one illustrative example, a laser bond inspection uses high-intensity stress waves to create a tensile load in test specimen strip 1708 during testing. Accordingly a portion of test specimen strip 1708 will be mechanically failed as part of the testing. As a result, a point on test specimen strip 1708 may be tested once.

However, the larger size of test specimen strip 1708 may allow for testing of multiple points on test specimen strip 1708 by inspection equipment. For example, a first point of test specimen strip 1708 may be tested by inspection equipment prior to testing a bond. A second point of test specimen strip 1708 may be tested by inspection equipment after testing a bond.

Smaller test specimen strips, test specimen strip 1704, test specimen strip 1706, test specimen strip 1710, and test specimen strip 1712, may be tested by mechanical testing equipment. Results of mechanically testing test specimen strip 1704, test specimen strip 1706, test specimen strip 1710, or test specimen strip 1712 may be used to determine the strength of the bond of test specimen assembly 1700.

As depicted, test specimen assembly 1700 comprises four smaller strips, test specimen strip 1704, test specimen strip 1706, test specimen strip 1710, and test specimen strip 1712. However, any combination of larger and smaller strips may be possible. In one illustrative example, test specimen assembly 1700 may instead comprise five larger strips and one smaller strip. In another illustrative example, test specimen assembly 1700 may have an equal number of larger and smaller strips. In yet another illustrative example, the plurality of test specimen strips 1702 may all be the same dimensions.

Although in this illustrative embodiment, larger test specimen strip 1708 is tested by non-destructive inspection equipment, test specimen strip 1704, test specimen strip 1706, test specimen strip 1710, or test specimen strip 1712 may be tested by non-destructive inspection equipment instead of or in addition to test specimen strip 1708. Also, although in this illustrative embodiment test specimen strip 1704, test specimen strip 1706, test specimen strip 1710, and test specimen strip 1712 may be mechanically tested, test specimen strip 1708 may be mechanically tested in addition to or instead of embodiment test specimen strip 1704, test specimen strip 1706, test specimen strip 1710, and test specimen strip 1712.

Figure 18:
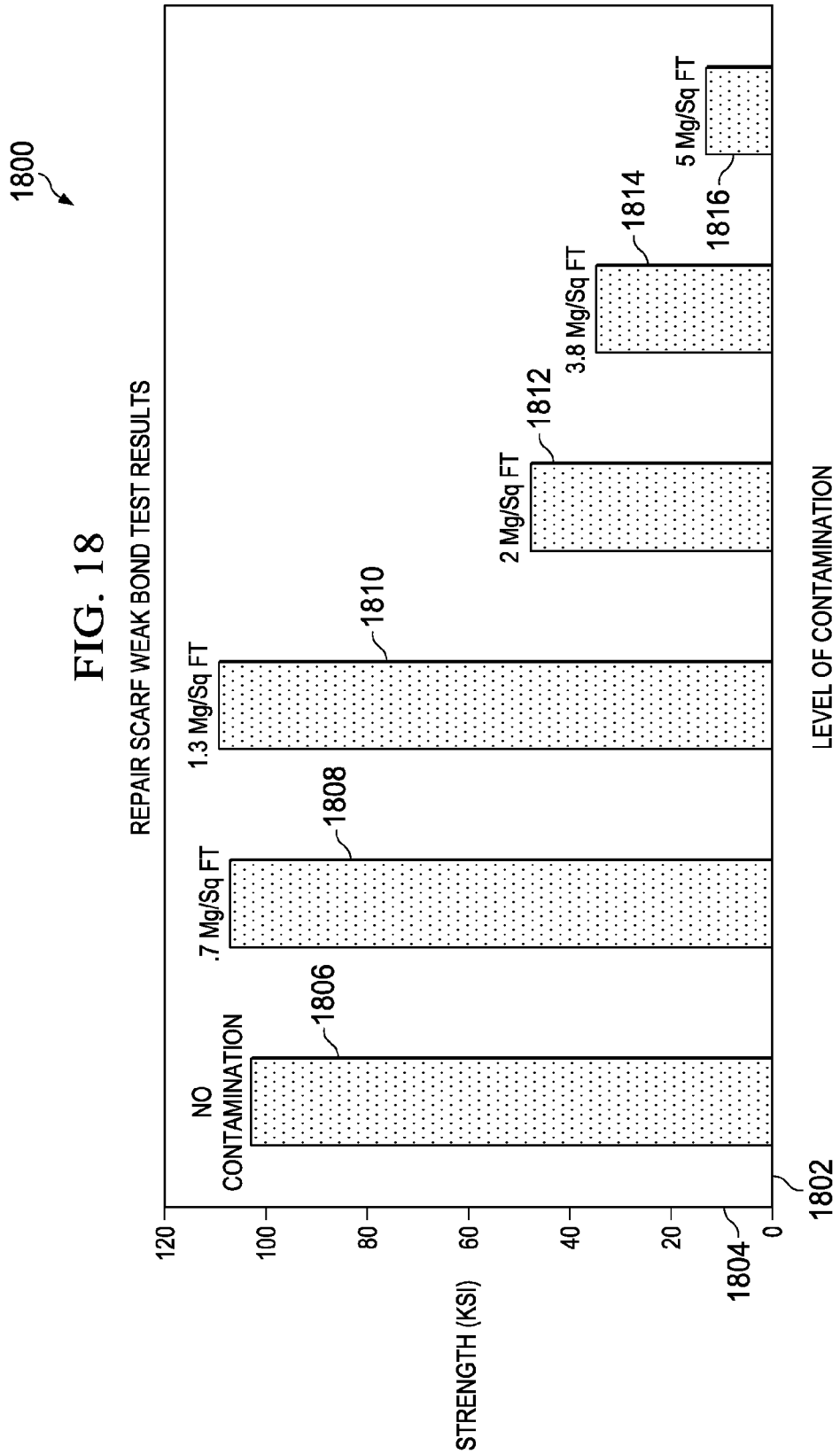
FIG. 18 is an illustration of a bar chart showing strength results of a plurality of test specimen assemblies prepared in accordance with an illustrative embodiment.

Turning now to FIG. 18, an illustration of a bar chart showing strength results of a plurality of test specimen assemblies prepared is depicted in accordance with an illustrative embodiment. FIG. 18 is an example of data for a test specimen assembly, such as test specimen assembly 102 shown in block form in FIG. 1. Bar chart 1800 has x-axis 1802 and y-axis 1804. As depicted, x-axis 1802 represents the surface treatment of the test specimen assembly in the form of the level of contamination applied. Similarly, y-axis 1804 represents bond strength measured in kilo pounds per square inch (KSI).

Bar 1806 represents a composite to composite scarf test specimen assembly with no surface treatment. As depicted, the desired strength for the test specimen assembly is about 103 KSI.

Bar 1808 represents a composite to composite scarf test specimen assembly with a surface treatment of about 0.7 milligram per square foot (Mg/Sqft) of release agent. In this example, the release agent applied to bar 1808, bar 1810, bar 1812, bar 1814, and bar 1816 is a Frekote® silicone release agent. As depicted, the surface treatment does not reduce the strength below desired strength.

Bar 1810 represents a composite to composite scarf test specimen assembly with a surface treatment of about 1.3 Mg/Sqft of release agent. As depicted, the surface treatment does not reduce the strength below desired strength.

Bar 1812 represents a composite to composite scarf test specimen assembly with a surface treatment of about 2 Mg/Sqft of release agent. As depicted, the surface treatment reduces the strength to about 48 KSI, or a ratio of about 0.50 of desired strength.

Bar 1814 represents a composite to composite scarf test specimen assembly with a surface treatment of about 3.8 Mg/Sqft of release agent. As depicted, the surface treatment reduces the strength to about 38 KSI, or a ratio of about 0.37 of desired strength.

Bar 1816 represents a composite to composite scarf test specimen assembly with a surface treatment of about 5 Mg/Sqft of release agent. As depicted, the surface treatment reduces the strength to about 13 KSI, or about a ratio of 0.15 of desired strength.

As can be seen in FIG. 18, strength, measured in KSI, decreases with applications of release agent greater than 1.3 Mg/Sq Ft. Table 11 (see Appendix) summarizes the selected contamination level treatments for creation of test specimen assemblies with varying bond strength. Contamination levels may be selected based on several criteria, including but not limited to reproducibility, percentage of desired strength, and manufacturing considerations.

Figure 19:
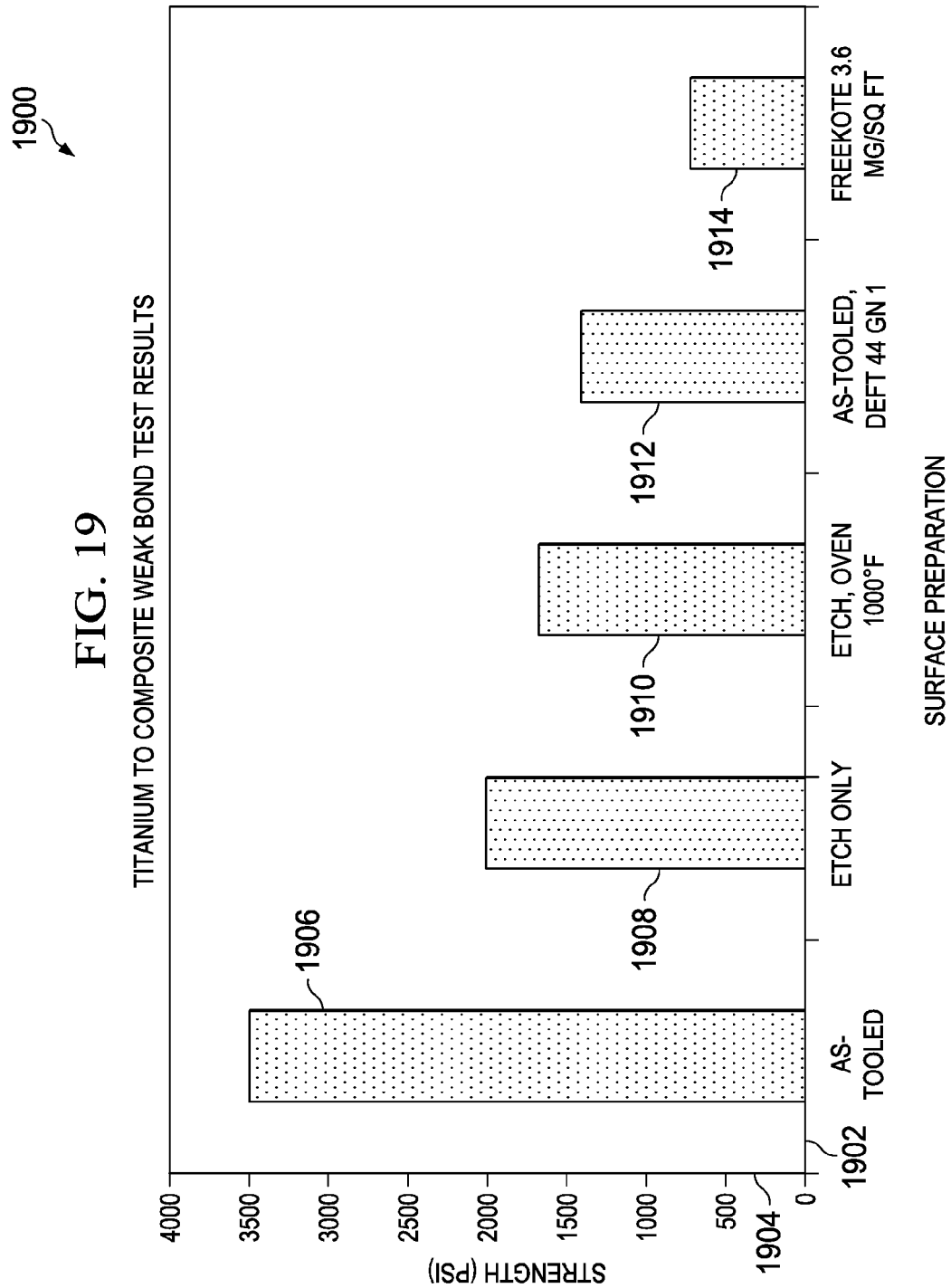
FIG. 19 is an illustration of a bar chart showing strength results of a plurality of test specimen assemblies prepared in accordance with an illustrative embodiment.

With reference next to FIG. 19, an illustration of another bar chart showing strength results of a plurality of test specimen assemblies prepared is depicted in accordance with an illustrative embodiment. FIG. 19 is an example of data for a test specimen assembly, such as test specimen assembly 102 shown in block form in FIG. 1. Bar chart 1900 has x-axis 1902 and y-axis 1904. As depicted, x-axis 1902 represents the surface treatment of the test specimen assembly. Similarly, y-axis 1904 represents bond strength measured in pounds per square inch (PSI).

In this illustrative example, titanium to composite test specimen assemblies are prepared with varying surface preparations. Surface preparations include etch, sol-gel, and primer; etch; etch and heating; etch, sol-gel and primer; and etch, sol-gel, primer, and release agent.

Bar 1906 represents a titanium to composite test specimen assembly with an as-tooled surface treatment. Prior to a surface treatment, the titanium surface is cleaned. The as-tooled surface treatment includes etch, sol-gel, and primer of the cleaned titanium surface. As depicted, the desired strength for the test specimen assembly is about 3500 PSI. Bar 1908 represents a titanium to composite test specimen assembly with a surface treatment of an etch of a cleaned titanium surface. In this illustrative example, the etch is a nitric-fluoride acid bath for five minutes. As depicted, the surface treatment of this etch reduces the strength to about 2000 PSI, or a ratio of about 0.57 of desired strength.

Bar 1910 represents a titanium to composite test specimen assembly with a surface treatment of an etch and heating at about 1000° F. of a cleaned titanium surface. As depicted, the surface treatment of this etch and heating reduces the strength to about 1700 PSI or a ratio of about 0.48 of desired strength.

Bar 1912 represents a titanium to composite test specimen assembly with a surface treatment of the as-tooled surface treatment of a cleaned titanium surface but with a different primer. In this illustrative embodiment, the etch and sol-gel are the same as the as-tooled surface treatment, however a different primer is used. The different primer is a DEFT 44 GN 1 primer in this illustrative example. As depicted, the surface treatment with this different primer reduces the strength to about 1400 PSI, or a ratio of about 0.40 of desired strength.

Bar 1914 represents a titanium to composite test specimen assembly with a surface treatment of the as-tooled surface treatment of a cleaned titanium surface followed by a release agent. The release agent applied to the test specimen assembly of bar 1914 is 3.6 Mg/Sq Ft of a Frekote® silicone release agent. As depicted, the surface treatment of this etch and heating reduces the strength to about 750 PSI, or a ratio of about 0.21 of desired strength.

As can be seen in FIG. 19, each of the different applied surface preparations results in a different strength, measured in PSI. Further, the difference in strength between each applied surface preparation is substantial. Accordingly, the bar chart appears as a series of well-defined steps downward. Such well-defined differences are desirable in identifying a range of strengths.

Figure 20:
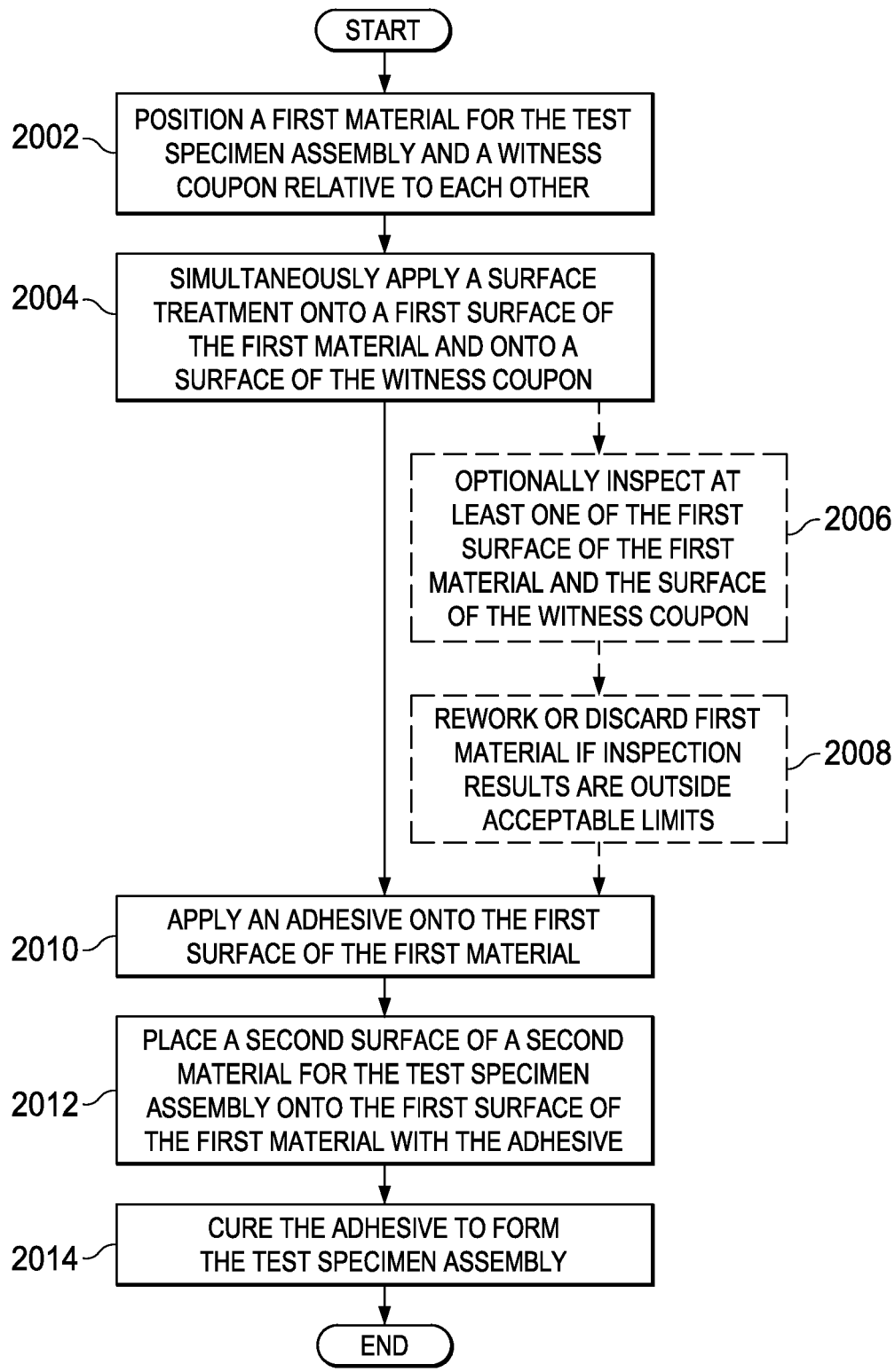
FIG. 20 is an illustration of a process for manufacturing a test specimen assembly, in the form of a flowchart, in accordance with an illustrative embodiment.

Turning now to FIG. 20, an illustration of a flowchart of a process for manufacturing a test specimen assembly is depicted in accordance with an illustrative embodiment. The process illustrated in FIG. 20 may be implemented in manufacturing environment 100 to manufacture test specimen assembly 102 in FIG. 1.

The process begins by positioning a first material for the test specimen assembly and a witness coupon relative to each other (operation 2002). The witness coupon may comprise the same or a different material than the first material for the test specimen. The process then simultaneously applies a surface treatment onto a first surface of the first material and onto a surface of the witness coupon (operation 2004).

Following application of the surface treatment, the process may optionally inspect at least one of the first surface of the first material and the surface of the witness coupon (operation 2006). Inspection of the first surface of the first material or witness coupon may generate a number of characteristics of the surface treatment applied to the first surface of the first material and the witness coupon.

By inspecting a witness coupon, the strength of a resulting bond may be indirectly identified. Additionally, if the material comprising the first material for the test specimen is difficult to inspect, the witness coupon may comprise a different, more easily inspected material. Further, the first material may continue to operation 2010 while witness coupon is inspected at operation 2006.

Following inspection, if the results of inspection are not acceptable, the first material may be reworked or discarded (operation 2008). If the witness coupon was inspected while the first material continued to processing, any resulting test specimen assembly would be reworked or discarded. Results of inspection may not be acceptable where characteristics of the applied surface treatment will not result in the intended ratio of desired bond strength. For example, the intended ratio of desired bond strength may be about 0.5. If the surface treatment is substantially thinner than necessary to produce a ratio of desired bond strength of about 0.5, the inspection results may not be acceptable.

If the inspection results are acceptable, the process proceeds to operation 2010 by applying an adhesive onto the first surface of the first material (operation 2010). Thereafter, the process places a second surface of a second material for the test specimen assembly onto the first surface of the first material with the adhesive (operation 2012). The process then cures the adhesive to form the test specimen assembly (operation 2014) with the process terminating thereafter.

Figure 21:
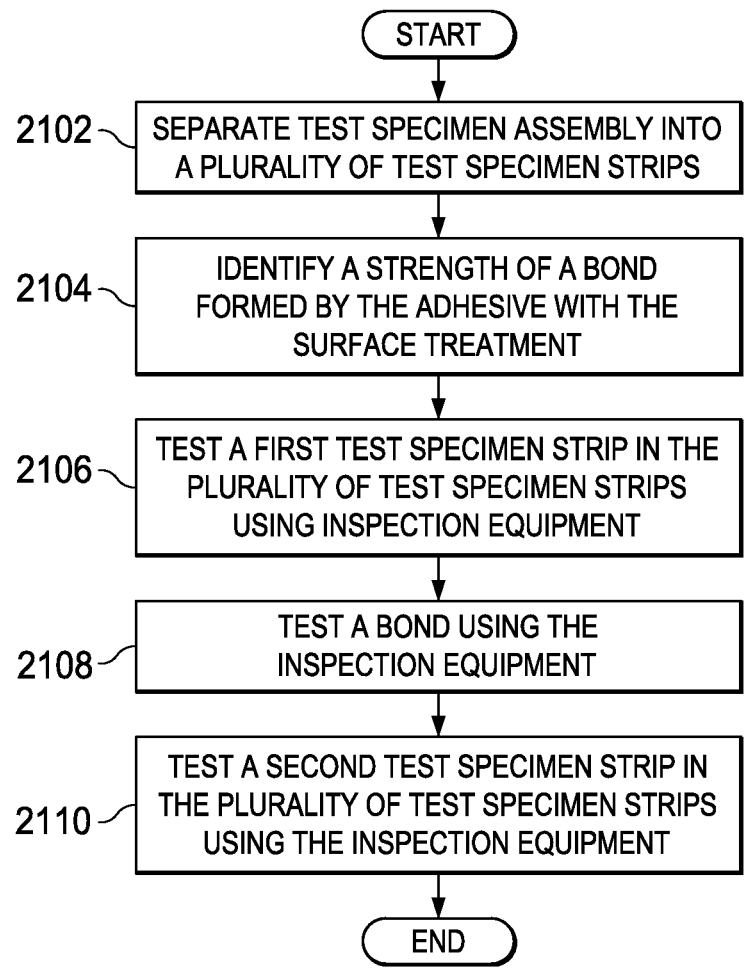
FIG. 21 is an illustration of a process for manufacturing a test specimen assembly, in the form of a flowchart, in accordance with an illustrative embodiment.

With reference next to FIG. 21, an illustration of a flowchart for a process for manufacturing a test specimen assembly is depicted in accordance with an illustrative embodiment. The process illustrated in FIG. 21 may be implemented in manufacturing environment 100 using inspection equipment 116 in FIG. 1.

The process begins by separating a test specimen assembly into a plurality of test specimen strips (operation 2102). The process may separate the test specimen assembly by cutting, scoring, bending, or any other suitable methods.

Next, the process identifies a strength of a bond formed by the adhesive with the surface treatment (operation 2104). The strength of the bond may be identified in several ways. If a witness coupon was present during processing, the strength of the bond may be identified based on a number of characteristics of the surface treatment which were formed on the surface of the witness coupon. Alternatively, the strength of the bond may be identified based on a number of characteristics of the surface treatment that were formed on the first surface of the first material. Additionally, the strength of the bond may be identified based on mechanically testing one of the plurality of test specimen strips.

The process then tests a first test specimen strip in the plurality of test specimen strips using inspection equipment (operation 2106). If the strength of the bond was previously identified using mechanical testing, this first test strip is a different test specimen strip than the one that was mechanically tested. During mechanical testing, the bond is broken. Accordingly, once mechanically tested, a test specimen strip cannot be reused.

After testing the first test specimen strip in the plurality of test specimen strips, the process tests a bond using the inspection equipment (operation 2108). After testing the bond, the process tests a second test specimen strip in the plurality of test specimen strips using the inspection equipment (operation 2110) with the process terminating thereafter.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, in FIG. 20, operation 2006 may occur after curing the adhesive to form the test assembly in operation 2014. Additionally, in FIG. 21, the strength of the bond may be identified in operation 2104 prior to separating the test specimen assembly into a plurality of test specimen assembly strips in operation 2102.

Utility of Disclosed Standards

Standards made using the techniques disclosed herein can be used as part of the certification of bonded structure where a validation of strength is required and a method of testing is used. When the bond strengths of these standards are measured, the results can demonstrate that the bond strength measurement technique used is sensitive to variations in bond strength and in calibration. The standards disclosed herein can be used to satisfy the FAA and DOD certification agencies that bonded structures are in fact strong because they provide a standard method to calibrate the methods for testing the bonds. The standards will be used in conjunction with the bonding assembly of FRP parts and the method of bond strength validation. The bond strength validation method will be tested on the standards prior to and after testing on the bonded assembly.

Figure 22:
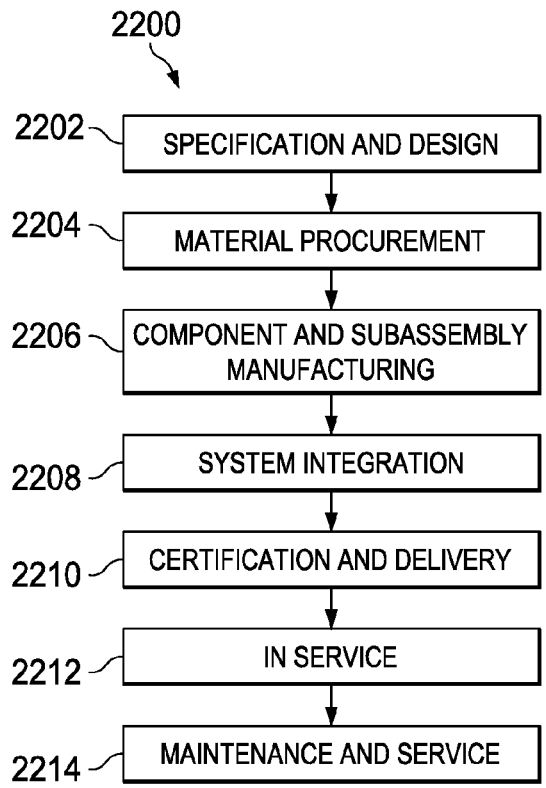
FIG. 22 is an illustration of an aircraft manufacturing and service method, in accordance with an illustrative embodiment.
Figure 23:
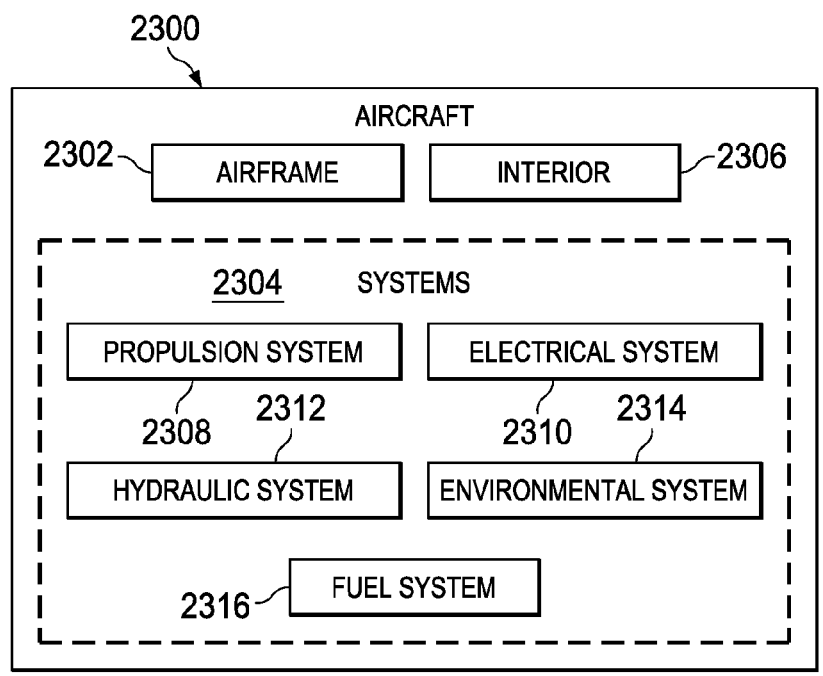
FIG. 23 is an illustration of an aircraft in which an illustrative embodiment may be implemented.

Illustrative embodiments of the disclosure may be described in the context of aircraft manufacturing and service method 2200 as shown in FIG. 22 and aircraft 2300 as shown in FIG. 23. Turning first to FIG. 22, an illustration of an aircraft manufacturing and service method is depicted in accordance with an illustrative embodiment. During pre-production, aircraft manufacturing and service method 2200 may include specification and design 2202 of aircraft 2300 in FIG. 23 and material procurement 2204.

During production, component and subassembly manufacturing 2206 and system integration 2208 of aircraft 2300 in FIG. 23 takes place. Thereafter, aircraft 2300 in FIG. 23 may go through certification and delivery 2210 in order to be placed in service 2212. While in service 2212 by a customer, aircraft 2300 in FIG. 23 is scheduled for routine maintenance and service 2214, which may include modification, reconfiguration, refurbishment, and other maintenance or service.

Each of the processes of aircraft manufacturing and service method 2200 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 23, an illustration of an aircraft is depicted in which an illustrative embodiment may be implemented. In this example, aircraft 2300 is produced by aircraft manufacturing and service method 2200 in FIG. 22 and may include airframe 2302 with plurality of systems 2304 and interior 2306. Examples of systems 2304 include one or more of propulsion system 2308, electrical system 2310, hydraulic system 2312, and environmental system 2314. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 2200 in FIG. 22. In one illustrative example, components or subassemblies produced in component and subassembly manufacturing 2206 in FIG. 22 may be fabricated or manufactured in a manner similar to components or subassemblies produced while aircraft 2300 is in service 2212 in FIG. 22. As another example, one or more apparatus embodiments, method embodiments, or a combination thereof may be utilized during production stages, such as component and subassembly manufacturing 2206 in FIG. 22 to test bonds. As yet another example, one or more apparatus embodiments, method embodiments, or a combination thereof may be utilized while aircraft 2300 is in service 2212 and/or during maintenance and service 2214 in FIG. 22 to test bonds. The use of a number of the different illustrative embodiments may substantially expedite the assembly of and/or reduce the cost of aircraft 2300.

Accordingly, the illustrative embodiments provide for repeatable methods of producing test specimen assemblies containing controlled levels of bond strength. Thus, test specimen assemblies may be formed without physical features or characteristics that may be detected by standard non-destructive inspection methods such as ultrasound, infrared, shearography, or x-ray. Additionally the test specimen assemblies may be formed in a repeatable manner so that additional test specimen assemblies may be made reliably and economically. Further, the illustrative embodiments provide for formation of test specimen assemblies with variable strength bonds from low ratios to desired strength. The test specimen assemblies may be adaptable to the thickness and surface slope of material used in actual construction.

Further, the illustrative embodiments may be implemented in testing non-destructive inspection methods to determine whether the method is able to detect bonds with lower than desired strength. The illustrative embodiments may also be implemented for calibration of a bond strength test method. The illustrative embodiments may be used to identify a setting for inspection equipment to detect a bond below a desired strength. Moreover, the illustrative embodiments may also be used to determine whether the inspection equipment is operating correctly to detect a bond below desired strength.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

APPENDIX

TABLE 1

| Type | Comment |
| --- | --- |
| Nylon 6,6 SRB (Super Release Blue) (Precision Fabrics 51789 FIN 061) | Nylon-based peel ply with inert, heat-stabilized cross-linked polymer finish (siloxane) |
| Nylon 6,6 (Precision Fabrics 51789) | Nylon-based peel ply fabric |
| Polyester peel ply BMS 8-308 (Precision Fabrics 60001) | Polyester-based peel ply fabric |

TABLE 2

| Peel Ply Type | WBPP1-CP1 | WBPP1-CP2 | WBPP1-CP3 | WBPP1-CP4 | WBPP1-CP5 | WBPP1-CP6 |
| --- | --- | --- | --- | --- | --- | --- |
| Polyester 600010 | 19.39 ± 1.02 | 19.54 ± 0.92 | 18.95 ± 0.68 | 19.14 ± 0.63 | 19.33 ± 0.64 | 19.27 ± 0.66 |
| Nylon 51789 | 19.88 ± 1.34 | 19.02 ± 0.67 | 19.08 ± 0.80 | 19.31 ± 0.73 | 19.01 ± 0.51 | 19.26 ± 0.58 |
| SRB 51789 | 20.11 ± 1.60 | 19.57 ± 0.88 | 18.91 ± 0.75 | 19.19 ± 0.55 | 19.16 ± 0.53 | 19.31 ± 0.60 |

TABLE 3

| Peel Ply Type | WBPP1-CP7 | WBPP1-CP8 | WBPP1-CP9 | WBPP1-CP10 | WBPP1-CP11 | WBPP1-CP12 |
| --- | --- | --- | --- | --- | --- | --- |
| Polyester 600010 | 19.47 ± 0.75 | 19.39 ± 0.74 | 19.36 ± 0.84 | 19.47 ± 0.65 | 19.54 ± 0.60 | 19.54 ± 0.77 |
| Nylon 51789 | 19.53 ± 1.00 | 19.66 ± 1.24 | 19.23 ± 1.32 | 19.16 ± 0.77 | 19.35 ± 0.88 | 19.34 ± 0.63 |
| SRB 51789 | 19.27 ± 1.22 | 19.31 ± 1.49 | 19.15 ± 1.20 | 18.97 ± 1.03 | 19.33 ± 1.03 | 19.11 ± 0.78 |

TABLE 4

| Peel Ply Type | WBPP1-CP1 | WBPP1-CP2 | WBPP1-CP3 | WBPP1-CP4 | WBPP1-CP5 | WBPP1-CP6 |
| --- | --- | --- | --- | --- | --- | --- |
| Polyester 600010 | 0.542 ± 0.046 | 0.563 ± 0.047 | 0.550 ± 0.043 | 0.551 ± 0.039 | 0.546 ± 0.039 | 0.557 ± 0.039 |
| Nylon 51789 | 0.547 ± 0.060 | 0.563 ± 0.049 | 0.550 ± 0.042 | 0.554 ± 0.045 | 0.541 ± 0.037 | 0.550 ± 0.042 |
| SRB 51789 | 0.566 ± 0.073 | 0.596 ± 0.052 | 0.520 ± 0.045 | 0.581 ± 0.049 | 0.555 ± 0.051 | 0.573 ± 0.048 |

TABLE 5

| Peel Ply Type | WBPP1-CP7 | WBPP1-CP8 | WBPP1-CP9 | WBPP1-CP10 | WBPP1-CP11 | WBPP1-CP12 |
| --- | --- | --- | --- | --- | --- | --- |
| Polyester 600010 | 0.566 ± 0.042 | 0.562 ± 0.033 | 0.554 ± 0.044 | 0.543 ± 0.044 | 0.559 ± 0.038 | 0.529 ± 0.039 |

TABLE 5-continued

| Peel Ply Type | WBPP1-CP7 | WBPP1-CP8 | WBPP1-CP9 | WBPP1-CP10 | WBPP1-CP11 | WBPP1-CP12 |
|---|---|---|---|---|---|---|
| Nylon 51789 | 0.568 ± 0.050 | 0.565 ± 0.062 | 0.558 ± 0.039 | 0.534 ± 0.047 | 0.541 ± 0.034 | 0.509 ± 0.039 |
| SRB 51789 | 0.593 ± 0.044 | 0.590 ± 0.051 | 0.566 ± 0.043 | 0.546 ± 0.046 | 0.557 ± 0.038 | 0.537 ± 0.038 |

TABLE 6

| Peel ply | DCB Relative $G_{1c}$ | Relative Lap Shear | Relative Trepanned Tensile Test |
|---|---|---|---|
| BMS 8-308 | 100 | 100 | 100 |
| Nylon | 14 | 62 | 80 |
| SRB | 7 | 33 | 64 |

TABLE 7

| Peel Ply Zone | Relative LBID Failure Power Level | Relative Lap Shear Strength | Relative DCB Ultimate Strength | Relative DCB $G_{1c}$ |
|---|---|---|---|---|
| SRB | 40 | 33 | 18 | 7 |
| Nylon | 65 | 62 | 32 | 14 |
| Polyester 600010 | 100 | 100 | 100 | 100 |

TABLE 8

| | Plasma Etch Level | |
|---|---|---|
| Sample Label | Plasma Gun Height | Plasma Gun Speed |
| PE0 | NA - as tooled surface | NA - as tooled surface |
| PE50 | 0.5 inch | 2 inches/second |
| PE75 | 0.5 inch | 0.5 inches/second |
| PE100 | 0.5 inch | 0.1 inches/second |

TABLE 9

| Sample | $G_{1c}$ (inch-lbs/inch$^2$) | Ultimate Load (lbs) |
|---|---|---|
| PE0 - As tooled | 0.43 ± 0.02 | 11.1 ± 0.9 |
| PE50 - 2 inches/sec | 1.5 (one sample) | 25.4 ± 4 |
| PE75 - 0.5 inch/sec | 7.2 ± 2.5 | 57 ± 07 |
| PE100 - 0.1 inch/sec | 11 ± 0.4 | 53 ± 7 |

TABLE 10

| Surface Preparation | Individual $G_{IC}$ Values (lb/in$^2$) | | | | | Avg. | St.Dev. |
|---|---|---|---|---|---|---|---|
| | 1 | 2 | 3 | 4 | 5 | | |
| Grit Blasting | 5.52 | 8.90 | 11.00 | 11.09 | 9.32 | 9.17 | 1.26 |
| Laser Etching | 4.23 | 6.26 | 6.74 | 6.55 | 5.60 | 5.88 | 1.02 |
| Plasma Etching 0.25" @ 0.5"/sec | 8.90 | 11.12 | 11.36 | 11.88 | 11.67 | 10.98 | 1.20 |
| Plasma Etching 0.25" @ 2.0"/sec | 2.60 | 4.67 | 4.95 | 6.04 | 5.82 | 4.81 | 1.38 |

TABLE 11

| Zone | Method |
|---|---|
| 1 | No contamination on scarfed sanded surface (full strength bond). |
| 2 | 2 Mg/Sq Ft release agent on scarfed sanded surface (~50% strength) |
| 3 | 5 Mg/Sq Ft release agent on scarfed sanded surface (~15% strength) |

What is claimed is:

1. A method for manufacturing a test specimen assembly comprising:
    positioning a first material for the test specimen assembly and a witness coupon relative to each other;
    applying a surface treatment onto a first surface of the first material and onto a surface of the witness coupon;
    applying an adhesive onto the first surface of the first material;
    placing a second surface of a second material for the test specimen assembly onto the first surface of the first material with the adhesive; and
    curing the adhesive to form the test specimen assembly.

2. The method of claim 1 further comprising:
    identifying a strength of a bond formed by the adhesive with the surface treatment based on a number of characteristics of the surface treatment formed on the surface of the witness coupon.

3. The method of claim 1, wherein the witness coupon comprises a material selected from one of a polished metal, a same material as the first material, and a different material than the first material.

4. The method of claim 1 further comprising:
    separating the test specimen assembly into a plurality of test specimen strips.

5. The method of claim 1 further comprising:
    testing the test specimen assembly using inspection equipment; and
    identifying a setting for the inspection equipment based on results from testing the test specimen assembly.

6. The method of claim 1, wherein the surface treatment is selected from at least one of contamination, etching, heating, a sol-gel, a primer, and a release agent.

7. The method of claim 1, wherein the first material is comprised of layers, and further comprising:
    exposing a number of the layers in the first material; and
    sanding the number of the layers exposed in the first material.

8. The method of claim 7, wherein the number of the layers exposed in the first material form a scarf for the first material.

9. The method of claim 1 further comprising:
    testing the test specimen assembly using inspection equipment following an inspection of a bond by the inspection equipment; and
    determining sensitivity of the inspection equipment based on results of testing the test specimen assembly.

10. The method of claim 4 further comprising:
identifying a strength of a bond formed by the adhesive with the surface treatment based on mechanically testing a first test specimen strip in the plurality of test specimen strips.

11. The method of claim 4 further comprising:
testing a first test specimen strip in the plurality of test specimen strips using inspection equipment;
testing a bond using the inspection equipment after testing the first test specimen strip; and
testing a second test specimen strip in the plurality of test specimen strips using the inspection equipment after testing the bond.

12. A test specimen assembly comprising:
a first material having a first surface, wherein the first surface has a surface treatment;
a second material having a second surface; and
an adhesive located between the first surface of the first material and the second surface of the second material wherein the adhesive forms a bond between the first material and the second material and a strength of the bond is reduced from a desired strength for the bond when the surface treatment is absent from the first surface.

13. The test specimen assembly of claim 12, wherein the surface treatment is selected from at least one of contamination, etching, heating, a sol-gel, a primer, and a release agent.

14. The test specimen assembly of claim 12, wherein the strength of the bond being reduced from the desired strength for the bond when the surface treatment is absent from the first surface is identifiable only by a strength measurement technique.

15. The test specimen assembly of claim 12, wherein the strength of the bond being reduced from the desired strength for the bond when the surface treatment is absent from the first surface is unidentifiable from inspection of the test specimen assembly using conventional non-destructive inspection equipment.

16. The test specimen assembly of claim 15, wherein the conventional non-destructive inspection equipment is selected from at least one of ultrasonic inspection equipment, infrared equipment, shearography, and x-ray inspection equipment.

17. The test specimen assembly of claim 12, wherein at least one of the first material and the second material comprise a metal.

18. The test specimen assembly of claim 12, wherein at least one of the first material and the second material comprise a composite.

19. The test specimen assembly of claim 12, wherein the first material comprises a plurality of layers and the first surface comprises a number of exposed and sanded layers in the plurality of layers in the first material.

20. A method for manufacturing a test specimen assembly comprising:
applying a surface treatment onto a first surface of a first material for the test specimen assembly, wherein the surface treatment is selected from at least one of contamination, etching, heating, a sol-gel, a primer, and a release agent;
identifying a strength of a bond formed by an adhesive with the surface treatment based on a number of characteristics of the surface treatment formed on the first surface;
applying the adhesive onto the first surface of the first material;
placing a second surface of a second material for the test specimen assembly onto the first surface of the first material with the adhesive; and
curing the adhesive to form the test specimen assembly.

* * * * *